(12) United States Patent
Hoyal-Wrightson et al.

(10) Patent No.: US 10,662,421 B2
(45) Date of Patent: *May 26, 2020

(54) METHODS AND COMPOSITIONS FOR THE EXTRACTION AND AMPLIFICATION OF NUCLEIC ACID FROM A SAMPLE

(71) Applicant: SEQUENOM, INC., San Diego, CA (US)

(72) Inventors: Carolyn R. Hoyal-Wrightson, San Diego, CA (US); Andreas Braun, San Diego, CA (US); Karsten E. Schmidt, San Diego, CA (US)

(73) Assignee: SEQUENOM, INC., San Diego, CA (US)

( * ) Notice: Subject to any disclaimer, the term of this patent is extended or adjusted under 35 U.S.C. 154(b) by 140 days.

This patent is subject to a terminal disclaimer.

(21) Appl. No.: 15/240,692

(22) Filed: Aug. 18, 2016

(65) Prior Publication Data

US 2017/0029807 A1 Feb. 2, 2017

Related U.S. Application Data

(60) Continuation of application No. 14/180,810, filed on Feb. 14, 2014, now Pat. No. 9,453,257, which is a division of application No. 12/301,985, filed as application No. PCT/US2007/069991 on May 30, 2007, now Pat. No. 8,679,741.

(60) Provisional application No. 60/810,228, filed on May 31, 2006, provisional application No. 60/807,061, filed on Jul. 11, 2006.

(51) Int. Cl.
*C12N 15/00* (2006.01)
*C12N 15/10* (2006.01)
*C12Q 1/6806* (2018.01)
*C12Q 1/686* (2018.01)

(52) U.S. Cl.
CPC ..... *C12N 15/1006* (2013.01); *C12N 15/1003* (2013.01); *C12N 15/1013* (2013.01); *C12Q 1/686* (2013.01); *C12Q 1/6806* (2013.01)

(58) Field of Classification Search
None
See application file for complete search history.

(56) References Cited

U.S. PATENT DOCUMENTS 4,656,127 A 4/1987 Mundy
4,683,195 A 7/1987 Mullis et al.
(Continued)

FOREIGN PATENT DOCUMENTS

EP 1 510 577 3/2005
EP 2414545 A2 2/2012
(Continued)

OTHER PUBLICATIONS

Jen (An overview on the isolation and analysis of circulating tumor DNA in plasma and serum, Ann N Y Acad Sci. Apr. 2000;906:8-12).*

(Continued)

*Primary Examiner* — Aaron A Priest
(74) *Attorney, Agent, or Firm* — Grant IP, Inc.

(57) ABSTRACT

Provided herein are methods, compositions and kits to extract and relatively enrich by physical separation or amplification short base pair nucleic acid in the presence of a high background of genomic material (e.g., host or maternal nucleic acids).

8 Claims, 5 Drawing Sheets

Specification includes a Sequence Listing.

Extraction of low base pair DNA in the presence of guanidine thiocyanate (GuSCN)

(56) References Cited

U.S. PATENT DOCUMENTS

| | | |
|---|---|---|
| 4,683,202 A | 7/1987 | Mullis |
| 4,851,331 A | 7/1989 | Vary et al. |
| 4,965,188 A | 10/1990 | Mullis et al. |
| 5,075,212 A | 12/1991 | Rotbart |
| 5,234,809 A | 8/1993 | Boom et al. |
| 5,346,994 A | 9/1994 | Chomczynski |
| 5,492,806 A | 2/1996 | Drmanac et al. |
| 5,525,464 A | 6/1996 | Drmanac et al. |
| 5,547,835 A | 8/1996 | Koster |
| 5,565,340 A | 10/1996 | Chenchik et al. |
| 5,589,330 A | 12/1996 | Shuber |
| 5,605,798 A | 2/1997 | Koster |
| 5,656,493 A | 8/1997 | Mullis et al. |
| 5,660,984 A | 8/1997 | Davis et al. |
| 5,679,524 A | 10/1997 | Nikiforov et al. |
| 5,691,141 A | 11/1997 | Koster |
| 5,695,940 A | 12/1997 | Drmanac et al. |
| 5,705,628 A | 1/1998 | Hawkins |
| 5,786,146 A | 7/1998 | Herman et al. |
| 5,834,189 A | 11/1998 | Stevens et al. |
| 5,849,483 A | 12/1998 | Shuber |
| 5,849,542 A | 12/1998 | Reeve et al. |
| 5,851,770 A | 12/1998 | Babon et al. |
| 5,869,242 A | 2/1999 | Kamb |
| 5,876,934 A | 3/1999 | Duthie et al. |
| 5,891,625 A | 4/1999 | Buchardt et al. |
| 5,898,071 A | 4/1999 | Hawkins |
| 5,908,755 A | 6/1999 | Kumar et al. |
| 5,912,118 A | 6/1999 | Ansorge et al. |
| 5,928,906 A | 7/1999 | Koster et al. |
| 5,958,692 A | 9/1999 | Cotton et al. |
| 5,976,802 A | 11/1999 | Ansorge et al. |
| 5,981,186 A | 11/1999 | Gabe et al. |
| 5,998,143 A | 12/1999 | Ellis et al. |
| 6,004,744 A | 12/1999 | Goelet et al. |
| 6,013,431 A | 1/2000 | Soderlund et al. |
| 6,013,438 A | 1/2000 | Didenko et al. |
| 6,013,499 A | 1/2000 | Narumiya et al. |
| 6,017,702 A | 1/2000 | Lee et al. |
| 6,018,041 A | 1/2000 | Drmanac et al. |
| 6,043,031 A | 3/2000 | Koster et al. |
| 6,045,996 A | 4/2000 | Cronin et al. |
| 6,046,005 A | 4/2000 | Ju et al. |
| 6,087,095 A | 7/2000 | Rosenthal et al. |
| 6,110,684 A | 8/2000 | Kemper et al. |
| 6,136,541 A | 10/2000 | Gulati |
| 6,140,054 A | 10/2000 | Wittwer et al. |
| 6,142,681 A | 11/2000 | Gulati |
| 6,156,501 A | 12/2000 | McGall et al. |
| 6,183,958 B1 | 2/2001 | Stanton, Jr. |
| 6,194,144 B1 | 2/2001 | Koster |
| 6,197,506 B1 | 3/2001 | Fodor et al. |
| 6,210,891 B1 | 4/2001 | Nyren et al. |
| 6,214,560 B1 | 4/2001 | Yguerabide et al. |
| 6,223,127 B1 | 4/2001 | Berno |
| 6,225,625 B1 | 5/2001 | Pirrung et al. |
| 6,229,911 B1 | 5/2001 | Balaban et al. |
| 6,229,991 B1 | 5/2001 | Hietala et al. |
| 6,239,273 B1 | 5/2001 | Pease et al. |
| 6,258,538 B1 | 7/2001 | Koster et al. |
| 6,274,351 B1 | 8/2001 | Peponnet |
| 6,274,726 B1 | 8/2001 | Laugharn et al. |
| 6,303,343 B1 | 10/2001 | Kopf-Sill |
| 6,383,393 B1 | 5/2002 | Colpan et al. |
| 6,534,262 B1 | 3/2003 | McKernan et al. |
| 6,596,480 B1 | 7/2003 | Didenko et al. |
| 6,723,513 B2 | 4/2004 | Lexow |
| 6,777,187 B2 | 8/2004 | Makarov et al. |
| 6,787,307 B1 | 9/2004 | Bitner et al. |
| 7,129,344 B1 | 10/2006 | Butt et al. |
| 7,169,314 B2 | 1/2007 | Unger et al. |
| 7,208,271 B2 * | 4/2007 | Bost .................. C12N 15/1006 435/6.16 |
| 7,226,739 B2 | 6/2007 | Ecker et al. |
| 7,255,992 B2 | 8/2007 | Ecker et al. |
| 8,679,741 B2 | 3/2014 | Hoyal-Wrightson et al. |
| 8,765,652 B2 | 7/2014 | Nelson et al. |
| 8,771,948 B2 | 7/2014 | Wisniewski |
| 9,371,556 B2 | 6/2016 | Nelson et al. |
| 9,453,257 B2 | 9/2016 | Hoyal-Wrightson et al. |
| 9,580,741 B2 | 2/2017 | Wisniewski et al. |
| 9,850,480 B2 | 12/2017 | Wisniewski et al. |
| 10,053,685 B2 | 8/2018 | Wisniewski et al. |
| 2003/0027135 A1 | 2/2003 | Ecker et al. |
| 2003/0044388 A1 | 3/2003 | Dennis et al. |
| 2003/0082539 A1 | 5/2003 | Ecker et al. |
| 2003/0082600 A1 | 5/2003 | Olek et al. |
| 2003/0092045 A1 | 5/2003 | Nargessi et al. |
| 2003/0124556 A1 | 7/2003 | Ecker et al. |
| 2003/0175695 A1 | 9/2003 | Ecker et al. |
| 2003/0175696 A1 | 9/2003 | Ecker et al. |
| 2003/0175697 A1 | 9/2003 | Ecker et al. |
| 2003/0180779 A1 | 9/2003 | Lofton-Day et al. |
| 2003/0190605 A1 | 10/2003 | Ecker et al. |
| 2004/0009518 A1 | 1/2004 | Lo et al. |
| 2004/0137449 A1 | 7/2004 | Nargessi |
| 2004/0137470 A1 | 7/2004 | Dhallan |
| 2004/0180328 A1 | 9/2004 | Ecker et al. |
| 2004/0209299 A1 | 10/2004 | Pinter et al. |
| 2004/0219517 A1 | 11/2004 | Ecker et al. |
| 2005/0019769 A1 | 1/2005 | Lenz |
| 2005/0053986 A1 | 3/2005 | Makarov et al. |
| 2005/0059024 A1 * | 3/2005 | Conrad .............. C12N 15/1003 435/6.12 |
| 2005/0112590 A1 | 5/2005 | Boom et al. |
| 2005/0164241 A1 | 7/2005 | Hahn et al. |
| 2005/0287583 A1 | 12/2005 | Smith et al. |
| 2005/0287592 A1 | 12/2005 | Kless |
| 2006/0019278 A1 | 1/2006 | Lo et al. |
| 2006/0024712 A1 | 2/2006 | Baker et al. |
| 2007/0048735 A1 | 3/2007 | Ecker et al. |
| 2007/0106071 A1 | 5/2007 | Yamashita et al. |
| 2007/0202511 A1 | 8/2007 | Chen et al. |
| 2007/0202525 A1 | 8/2007 | Quake et al. |
| 2008/0139800 A1 | 6/2008 | Deggerdal et al. |
| 2008/0166703 A1 | 7/2008 | Himmelreich et al. |
| 2008/0305479 A1 | 12/2008 | Van Den Boom |
| 2009/0018323 A1 | 1/2009 | Erbacher et al. |
| 2009/0202984 A1 | 8/2009 | Cantor |
| 2010/0297710 A1 | 11/2010 | Hoyal-Wrightson et al. |
| 2012/0178918 A1 | 7/2012 | Wisniewski et al. |
| 2014/0255943 A1 | 9/2014 | Hoyal-Wrightson et al. |
| 2014/0349291 A1 | 11/2014 | Wisniewski et al. |
| 2017/0029807 A1 | 2/2017 | Hoyal-Wrightson et al. |
| 2017/0198278 A1 | 7/2017 | Wisniewski et al. |
| 2018/0073010 A1 | 3/2018 | Wisniewski et al. |
| 2019/0010486 A1 | 1/2019 | Wisniewski et al. |

FOREIGN PATENT DOCUMENTS

| | | |
|---|---|---|
| WO | WO 97/037041 | 10/1997 |
| WO | WO 98/020019 | 5/1998 |
| WO | WO 99/029905 | 6/1999 |
| WO | WO 99/058664 | 11/1999 |
| WO | WO 00/052625 | 9/2000 |
| WO | WO 01/020039 | 3/2001 |
| WO | WO 01/025485 | 4/2001 |
| WO | WO 01/027327 | 4/2001 |
| WO | WO 01/027329 | 4/2001 |
| WO | WO 01/029259 | 4/2001 |
| WO | WO 03/040687 | 5/2003 |
| WO | WO 04/108925 | 12/2004 |
| WO | WO 05/023091 | 3/2005 |
| WO | WO 06/056480 | 6/2006 |
| WO | WO 07/069991 | 6/2007 |
| WO | WO 07/140417 | 12/2007 |
| WO | WO 07/147063 | 12/2007 |
| WO | WO 09/032779 | 3/2009 |
| WO | WO 09/032781 | 3/2009 |

(56) References Cited

FOREIGN PATENT DOCUMENTS

| | | |
|---|---|---|
| WO | WO 09/091934 | 7/2009 |
| WO | WO 10/115016 | 10/2010 |

OTHER PUBLICATIONS

Van der Hel (Quality and quantity of DNA isolated from frozen urine in population-based research, Anal Biochem. May 15, 2002;304 (2):206-11).*
ThermoFisher (Sodium Acetate Precipitation of Small Nucleic Acids, available at https://www.thermofisher.com/us/en/home/references/protocols/nucleic-acid-purification-and-analysis/dna-protocol/sodium-acetate-precipitation-of-small-nucleic-acids.html, Mar. 18, 2005).*
Budelier (Purification of DNA by Anion-Exchange Chromatography, Curr Protoc Mol Biol. May 2001;Chapter 2:Unit2.1B).*
Herzer (DNA Purification, in Molecular Biology Problem Solver: A Laboratory Guide, Edited by Alan S. Gerstein, Ch. 7, pp. 167-195, Dec. 31, 2001).*
Allemand et al., "pH-dependent specific binding and combing of DNA" Biophys. Journal (1997) 73:2064-2070.
Amicucci P., et al., "Prenatal diagnosis of myotonic dystrophy using fetal DNA obtained from maternal plasma" Clin. Chem. (2000) 46:301-302.
Anantha et al., "Porphyrin binding to quadrupled T4G4." Biochemistry. Mar. 3, 1998;37(9):2709-14.
Anker P and Stroun M, Clin Chem (2002) 48, 1210-1211.
Anker P, et al. Cancer Metastasis Rev (1999) 18, 65-73.
Applied Biosystems, "Transitioning from Standard to Fast PCR on the Applied Biosystems 9800 Fast PCR System" Applied Biosystems Data Sheet (2005).
Atamaniuk et al., "Cell-Free Plasma DNA: A Marker for Apoptosis during Hemodialysis" Clin. Chem (2006) 52(3):523-6.
Beaucage and Caruthers, Tetrahedron Letts., 22:1859-1862, 1981.
Birnboim et al., "A rapid alkaline extraction procedure for screening recombinant plasmid DNA," Nucleic Acids Research, 1979, vol. 7, No. 6, pp. 1513-1523.
Bischoff et al., "Cell-Free Fetal DNA and Intact Fetal Cells in Maternal Blood Circulation: Implications for First and Second Trimester Non-Invasive Prenatal Diagnosis," Human Reproductive Update, Oxford University Press vol. 8, No. 6, pp. 493-500, Nov. 1, 2002.
Bischoff et al., Hum Reprod Update. Jan.-Feb. 2005;11(1):59-67.
Braslavsky et al., "Sequence information can be obtained from single DNA molecules." Proc Natl Acad Sci U S A. Apr. 1, 2003;100(7):3960-4.
Chan et al, Clin Chem. Jan. 2004;50(1):88-92.
Chan KC and Lo YM, Histol Histopathol (2002) 17,937-943.
Chen et al., "Fluorescence energy transfer detection as a homogeneous DNA diagnostic method." Proc Natl Acad Sci U S A. Sep. 30, 1997;94(20):10756-61.
Chen et al., "Template-directed dye-terminator incorporation (TDI) assay: a homogeneous DNA diagnostic method based on fluorescence resonance energy transfer." Nucleic Acids Res. Jan. 15, 1997;25(2):347-53.
Chen XQ, et al. Nat Med (1996) 2,1033-1035.
Chiu RWK, et al. (2002) Lancet 360:998-1000.
Choi et al., "Release of DNA from Dead and Dying Lymphocyte and Monocyte Cell Lines In Vitro" Scand. J. Immunol. (2004) 60:159-66.
Clontech. ApoAlert. LM-PCR Ladder Assay Kit User Manual, Aug. 17, 2001 pp. 1-14.
Costa JM, Ernault P (2002) Clin Chem 48:679-680.
Costa JM, et al. Prenat Diagn 21:1070-1074.
Current Protocols in Molecular Biology, John Wiley & Sons, N.Y., 6.3.1-6.3.6 (1989).
Dear PH., "One by one: Single molecule tools for genomics." Brief Funct Genomic Proteomic. Jan. 2003;1(4):397-416.

Definition of Whole Blood by the Free Online Dictionary, Thesaurus and Encyclopedia available at: http://www.thefreedictionary.com/whole+blood.
Dhallan et al., "Methods to Inrease the Percentage of Free Fetal DNA Recovered from the Maternal Circulation," JAMA The Journal of the American Medical Association, vol. 291, No. 9, pp. 1114-1119, Mar. 1, 2004.
Didenko et al, "Early necrotic DNA degradation: presence of blunt-ended DNA breaks, 3' and 5' overhangs in apoptosis, but only 5' overhangs in early necrosis," Am J Pathol. May 2003;162(5):1571-1578.
Egger et al., "Reverse transcription multiplex PCR for differentiation between polio- and enteroviruses from clinical and environmental samples." J Clin Microbiol. Jun. 1995;33(6):1442-7.
European Search Report, dated Apr. 16, 2010 in European Application No. 07797885.6.
Extended European Search Report dated May 14, 2013 in European Patent Application No. EP12196349 filed: May 31, 2007.
Finning KM, et al. (2002) Transfusion 42:1079-1085.
Fournie et al., Cancer Lett 1995;91:221-227.
Fournie et al., Gerontology 1993;39:215-221.
Fucharoen G, et al. (2003) Prenat Diagn 23:393-396.
Geneclean: Gel Isolation and Reaction Cleanup Information Flyer, Qbiogene, Inc. 2002.
Gonzalez-Gonzalez MC, et al. (2002) Prenat Diagn 22:946-948.
Gonzalez-Gonzalez MC, et al. (2003) Prenat Diagn 23:232-234.
Goya et al., "Glucocorticold-induced apoptosis in lymphoid organs is associated with a delayed increase in circulating deoxyribonucleic acid" Apoptosis (2003) 8(2):171-177.
Grompe et al., Proc. Natl. Acad. Sci. USA 86: 5888-5892 (1989).
Grompe, Nature Genetics 5: 111-117 (1993).
Haase et al., Methods in Virology, pp. 189-226, 1984, Academic Press, Maramorusch et al. (eds.).
Hames and Higgins eds., Nucleic Acid Hybridization: A Practical Approach, IRL Press, 1987 pp. vii-xv and 1-2.
Harris et al., "Single-molecule DNA sequencing of a viral genome." Science. Apr. 4, 2008;320(5872):106-9.
Herzer, Molecular Biology Problem Solver: A Laboratory Guide, Chapter 7 "DNA Purification" pp. 167-195, Alan S. Gerstein, ed., Wiley-Liss, Inc. (2001).
IDT, Modified Bases Modifications, available at http://www.idtdna.com/site/Catolog/Modifications/Category/7, Jul. 31, 2004.
Ikeda et al., "Apoptosis in cumulus cells during in vitro maturation of bovine cumulis-enclosed oocytes," Reproduction, vol. 125, Jan. 1, 2003, pp. 369-376.
Illanes et al., "Cell-free fetal DNA in maternal plasma: an important advance to link fetal genetics to obstetric ultrasound" Ultrasound in Obstetrics & Gynecology (2005) 25(4):317-322.
ImageMaster VDS, Application Note #1, Imaging DNA Agarose Gels Stained with Ethidium Bromide, Amersham Biosciences, Aug. 1996.
International Search Report and Written Opinion dated Dec. 19, 2007 for PCT/US2007/069991 and published as: WO2007/140417 on Dec. 6, 2007.
International Search Report and Written Opinion dated Jan. 31, 2011, for International Application No. PCT/US2010/029653, filed Apr. 10, 2010 and published as WO/2010/029653 on Mar. 18, 2010.
Jahr S, et al. Cancer Res (2001) 61,1659-1665.
Jurinke et al., "MALDI-TOF mass spectrometry: a versatile tool for high-performance DNA analysis." Mol Biotechnol. Feb. 2004;26(2):147-64.
Kalinina et al., "Nanoliter scale PCR with TaqMan detection." Nucleic Acids Res. May 15, 1997;25(10):1999-2004.
Lichtenstein et al., "Circulating Nucleic Acids and Apoptosis" Ann. NY Acad. Sci. (2001) 945:239-249.
Li et al, "Whole genome amplification of plasma-circulating DNA enables expanded screening for allelic imbalance in plasma," J Mol Diagn. Feb. 2006;8(1):22-30.
Li et al, Clin Chem. Jun. 2004;50(6):1002-1011.
Lo et al. (1998) N Engl J Med 339:1734-1738.
Lo et al. Am J Hum Genet (1999) 64:218-224.

(56) References Cited

OTHER PUBLICATIONS

Lo et al., "Quantitative Analysis of Fetal DNA in Maternal Plasma and Serum: Implications for Noninvasive Prenatal Diagnosis," American Journal of Human Genetis, vol. 62, No. 4, pp. 768-775, Apr. 1, 1998.
Lo et al., Clin Chem 2000;46:319-323.
Lo et al., Lancet 1998;351:1329-1330.
Lo KW, et al. Clin Chem (1999) 45,1292-1294.
Lo YM, "Fetal nucleic acids in maternal plasma." Ann N Y Acad Sci. Aug. 2008;1137:140-3.
Lo YM, "Recent advances in fetal nucleic acids in maternal plasma." J Histochem Cytochem. Mar. 2005;53(3):293-6.
Margulies et al., "Genome sequencing in microfabricated high-density picolitre reactors." Nature. Sep. 15, 2005;437(7057):376-80.
Maxim Biotech (PCR Kits for DNA Ladder Assay (Cat. #: APO-DNA1), Feb. 15, 2000.
MirVana miRNA Isolation Kit, Ambion, 2006.
Nagata, "Apoptotic DNA Fragmentation" Experimental Cell Research (2000) 256:12-18.
Nakano et al., "Single-molecule PCR using water-in-oil emulsion." J Biotechnol. Apr. 24, 2003;102(2):117-24.
Nawroz H et al., Nat Med 1996;2:1035-1037.
Needham-VanDevanter et al., "Characterization of an adduct between CC-1065 and a defined oligodeoxynucleotide duplex." Nucleic Acids Res. Aug. 10, 1984;12(15):6159-68.
Ng EK, et al. Proc Natl Acad Sci USA (2003) 100, 4748-4753.
Nolte FS., "Branched DNA signal amplification for direct quantitation of nucleic acid sequences in clinical specimens." Adv Clin Chem. 1998;33:201-35.
Oeth, P. et al., "iPLEX™ Assay: Increased Plexing Efficiency and Flexibility for MassARRAY® System through single base primer extension with mass-modified Terminators." SEQUENOM Application Note (2005).
Orita et al., Proc. Natl. Acad. Sci. U.S.A 86: 2766-2770 (1989).
PCR Protocols: A Guide to Methods and Applications, Innis et al., eds, 1990 pp. v-x.
Pearson and Regnier, J. Chrom., 255:137-149, 1983.
Pichl et al., "Magnetic bead technology in viral RNA and DNA extraction from plasma minipools," Transfusion Complications, Jul. 2005, vol. 45, pp. 1106-1110.
Qiagen AllPrep DNA/RNA Mini Handbook, Nov. 2005.
Qiagen QIAamp DNA Mini Kit and QIAamp DNA Blood Mini Kit Handbook, Sep. 2001.
Qu et al., "Analysis of drug-DNA binding data." Methods Enzymol. 2000;321:353-69.
Rijnders RJ, et al. (2001) Obstet Gynecol 98:374-378.
Romero and Rotbart in Doagnostic Molecular Biology: Principles and Applications pp. 401-406, Persing et al., eds., Mayo Foundation, Rochester, Minn., 1993.
Rumore and Steinman J Clin Invest. Jul. 1990;86(1):69-74.
Saito H, et al. (2000) Lancet 356:1170.
Saiyed et al., "Applicaiton of magnetic techniques in the field of drug discovery and biomedicine" BioMagnetic Research and Technology (2003) 1:1-8.
Sambrook and Russell, Molecular Cloning: A Laboratory Manual 3d ed., 2001 pp. v-xx.
Schmidt et al., "Detection and direct genomic sequencing of multiple rare unknown flanking DNA in highly complex samples" Human Gene Therapy (2001) 12(7):743-749.
Sheffield et al., Proc. Natl. Acad. Sci. USA 49: 699-706 (1991).
Shiels et al., "MagneSil, C'est Magnifique!" Promega Notes (2001) 79:22-24.
Singer et al., Biotechniques 4:230, 1986.
Slor, "A new assay of deoxyribnucleases using as a substrate radioactively labeled DNA bound either directly or through anti-DNA antibodies to plastic depression plates" Nucleic Acids Research (1975) 2(5):745-756.
Soni et al., "Progress toward ultrafast DNA sequencing using solid-state nanopores." Clin Chem. Nov. 2007;53(11):1996-2001.
Staley et al, Cell Death Differ. Jan. 1997;4(1):66-75.
Stroun et al., "About the possible origin and mechanism of circulating DNA Apoptosis and active DNA release" Clin. Chim. Acta. (2001) 313(1-2):139-142.
Stroun M, et al. Oncology (1989) 46,318-322.
Supplementary European Search Report dated Dec. 18, 2013 in European Patent Application No. 10759416.0, filed on Apr. 1, 2010 and published as EP 2 414 545.
Thomas, "Hybridization of denatured RNA and small DNA fragments transferred to nitrocellulose" PNAS USA (1980) 77(9):5201-5205.
Vaickus et al., "Immune markers in hematologic malignancies." Crit Rev Oncol Hematol. Dec. 1991;11(4):267-97.
Venter et al., "The sequence of the human genome." Science. Feb. 16, 2001;291(5507):1304-51.
Vincent et al., "Helicase-dependent isothermal DNA amplification." EMBO Rep. Aug. 2004;5(8):795-800.
Vogelstein et al., "Digital PCR." Proc Natl Acad Sci U S A. Aug. 3, 1999;96(16):9236-41.
Vogelstein et al., "Preparative and analytical purification of DNA from agarose" PNAS USA (1979) 76(2):615-619.
Wang et al. Clin Chem. Jan. 2004;50(1):211-213.
White et al., Genomics 12: 301-306 (1992).
Widlak et al, J Biol Chem. Mar. 17, 2000;275(11):8226-8232.
Xu et al., "Immobilization of DNA on an Aluminum(III) Alkanebisphosphonate Thin Film with Electrogenerated Chemiluminescent Detection" J. Am. Chem. Soc. (1994) 116(18):8386-8387.
Office Action dated Dec. 13, 2012 in U.S. Appl. No. 12/301,985, filed Aug. 9, 2010 and published as: 2010/0297710 on Nov. 25, 2010.
Office Action dated Jun. 3, 2013 in U.S. Appl. No. 12/301,985, filed Aug. 9, 2010 and published as US 2010/0297710 on Nov. 25, 2010.
Office Action dated Nov. 5, 2013 in U.S. Appl. No. 12/301,985, filed Aug. 9, 2010 and published as US 2010/0297710 on Nov. 25, 2010.
Office Action dated Oct. 11, 2013 in U.S. Appl. No. 13/262,624, filed Mar. 1, 2012 and published as US 2012/0178918 on Jul. 12, 2012.
Office Action dated Mar. 14, 2014 in U.S. Appl. No. 13/262,624, filed Mar. 1, 2012 and published as US 2012/0178918 on Jul. 12, 2012.
Office Action dated Jul. 17, 2015 in U.S. Appl. No. 14/180,810, filed Feb. 14, 2014 and published as US 2014-0255943 on Sep. 11, 2014.
Office Action dated Dec. 18, 2015 in U.S. Appl. No. 14/180,810, filed Feb. 14, 2014 and published as US 2014-0255943 on Sep. 11, 2014.
Office Action dated Mar. 11, 2016 in U.S. Appl. No. 14/296,732, filed Jun. 5, 2014 and published as US 2014-0349291 on Nov. 27, 2014.
Office Action dated May 18, 2016 in U.S. Appl. No. 14/180,810, filed Feb. 14, 2014 and published as US 2014-0255943 on Sep. 11, 2014.
Office Action dated Aug. 9, 2016 in U.S. Appl. No. 14/296,732, filed Jun. 5, 2014 and published as US 2014-0349291 on Nov. 27, 2014.
Office Action dated Oct. 24, 2016 in U.S. Appl. No. 14/296,732, filed Jun. 5, 2014 and published as US 2014-0349291 on Nov. 27, 2014.
Extended European Search Report dated May 31, 2017 in European Patent Application No. 16203716.2, filed on Apr. 1, 2010.
Ying-Hsiu Su et al., "Removal of High-Molecule-Weight DNA by Carboxylated Magnetic Beads Enhances the Detection of Mutated K-ras DNA in Urine" Ann. NY Acad. Sci. (2008) 1137:82-91.
Office Action dated Jun. 6, 2017 in U.S. Appl. No. 15/409,189, filed Jan. 18, 2017.
Office Action dated Aug. 16, 2017 in U.S. Appl. No. 15/409,189, filed Jan. 18, 2017 and published as US 2017/0198278 on Jul. 13, 2017.
Extended European Search Report dated Oct. 27, 2017 in European Patent Application No. 17180962.7, filed on May 30, 2007 and published as EP 3 260 566 on Dec. 27, 2017.
Office Action dated Dec. 14, 2017 in U.S. Appl. No. 15/813,979, filed Nov. 15, 2017 and published as US 2018/0073010 on Mar. 15, 2018.

(56) References Cited

OTHER PUBLICATIONS

Office Action dated Apr. 23, 2018 in U.S. Appl. No. 15/813,979, filed Nov. 15, 2017 and published as US 2018/0073010 on Mar. 15, 2018.
Extended European Search Report dated Mar. 29, 2019 in European Patent Application No. 18214114.3, filed on Apr. 1, 2010.
"International Preliminary Report on Patentability dated Dec. 18, 2008 in International Patent Application No. PCT/US2007/069991, filed on May 30, 2007", 10 pages.
"International Preliminary Report on Patentability dated Oct. 13, 2011 in International Patent Application No. PCT/US2010/029653, filed on Apr. 1, 2010", 7 pages.
Lo, et al. "Presence of Fetal DNA in Maternal Plasma and Serum", The Lancet, 1997, 350(906):485-487.

* cited by examiner

Extraction of low base pair DNA in the presence of guanidine thiocyanate (GuSCN)

Extraction of low base pair DNA in the presence of sodium perchlorate (NaClO$_4$)

Circular ligation and inverse PCR

METHODS AND COMPOSITIONS FOR THE EXTRACTION AND AMPLIFICATION OF NUCLEIC ACID FROM A SAMPLE

RELATED PATENT APPLICATIONS

This patent application is a continuation of U.S. patent application Ser. No. 14/180,810, filed on Feb. 14, 2014, entitled "Methods and Compositions for the Extraction and Amplification of Nucleic Acid from a Sample," naming Carolyn R. Hoyal-Wrightson, Andreas Braun, and Karsten E. Schmidt as inventors; which is a divisional of U.S. patent application Ser. No. 12/301,985, now U.S. Pat. No. 8,679,741, filed on Aug. 9, 2010, entitled "Methods and Compositions for the Extraction and Amplification of Nucleic Acid from a Sample," naming Carolyn R. Hoyal-Wrightson, Andreas Braun, and Karsten E. Schmidt as inventors; which is a national stage of international patent application number PCT/US2007/069991, filed on May 30, 2007, entitled "Methods and Compositions for the Extraction and Amplification of Nucleic Acid From a Sample," naming Carolyn R. Hoyal-Wrightson, Andreas Braun, and Karsten E. Schmidt as inventors; which claims the benefit of U.S. provisional patent application Nos. 60/810,228 and 60/807,061, filed on May 31, 2006 and Jul. 11, 2006, respectively, each entitled "Methods and Compositions for the Extraction and Amplification of Nucleic Acid from a Sample," respectively. The entire content of each of the foregoing patent applications hereby is incorporated by reference herein, including all text, drawings and tables, in jurisdictions providing for such incorporation.

SEQUENCE LISTING

The instant patent application contains a Sequence Listing that has been submitted via EFS-Web and is hereby incorporated by reference in its entirety. The ASCII copy, created on Jan. 23, 2009, is named SEQ-6001-US.txt and is 1,234 bytes in size.

FIELD OF THE INVENTION

The invention relates to methods and kits for the extraction, and optionally the amplification, of nucleic acids from a sample, particularly from a biological sample containing cell-free nucleic acids. The methods of the invention may be used in a wide range of applications, including the extraction of fetal nucleic acids from maternal plasma, the detection of circulating nucleic acids from neoplasms (malignant or non-malignant), the detection of early onset of tissue rejection, or any other application requiring the selective separation of nucleic acids based on their size and/or apoptotic origin.

BACKGROUND

The isolation and subsequent amplification of nucleic acids play a central role in molecular biology. Isolated, purified nucleic acids may be used, inter alia, as a starting material for diagnosis and prognosis of diseases or disorders. Therefore, the isolation of nucleic acids, particularly by non-invasive means, is of particular importance for use in genetic analyses.

Current methods for the extraction of nucleic acids include the use of organic-based methods (e.g., phenol/chloroform/isoamyl alcohol), or capitalize upon ion interaction of nucleic acids in an aqueous solution (e.g., salting out in combination with alcohol, solution pH and temperature) alone or in combination with anion exchange chromatography or cation exchange chromatography. Organic-based methods employ the use of phenol/chloroform/isoamyl alcohol or variations thereof for isolating DNA, but have serious disadvantages, namely the processes are very time-consuming, require considerable experimental effort, and are associated with an acute risk of exposure to toxic substances to those carrying out the isolation. Chromatography-based methods increase flexibility and automation since these methods can be used in combination with multiple matrices (e.g., membranes, latex, magnetic beads, micro-titer plate, etc.) and in the presence or absence of ligands (e.g., DEAE, silica, acrylamide, etc.). However, these methods are better suited to extract larger strands of nucleic acids to ensure greater success in downstream analysis.

Previously, the recovery of smaller, fragmented nucleic acids from biological samples was considered unimportant, and extraction methods were designed to isolate large, undegraded nucleic acid molecules. Recently, however, it is shorter base pair nucleic acids (e.g., highly degraded RNA or mRNA and apoptotic DNA) that have been shown to be highly informative for a wide range of applications, including prenatal diagnostics and the study of apoptotic DNA from host or non-host sources. Methods to capture and protect RNA during extraction are now common; however the ability to successfully analyze short, fragmented DNA in the presence of more abundant, longer DNA has remained elusive.

SUMMARY OF THE INVENTION

There is a need for improved extraction methods capable of capturing small nucleic acid molecules. At the same time, these methods need to be simple, cost-effective and automatable in order to prove useful in the research and clinical environments. Thus, in one aspect, the invention relates to compositions, methods and kits for the extraction, amplification and analysis of nucleic acids based on their size. Studies have shown that the majority of cell-free nucleic acid resulting from neoplasms, allograft rejection, autoimmune reactions, fetal tissue, etc. has a relatively small size of approximately 1,200 base pairs or less, whereas the majority of cell-free nucleic acid arising in the host from non-programmed cell death-associated events has a size greater than approximately 1,200 base pairs.

The present invention, therefore, provides compositions, methods and kits for the enrichment, based on size discrimination, of nucleic acid of approximately 1,200 base pairs or less (herein referred to as "target nucleic acid") in a high background of genomic nucleic acid (herein referred to as "non-target nucleic acid"). This leads to a relatively enriched fraction of nucleic acid that has a higher concentration of smaller nucleic acid.

The present invention provides methods for extracting target nucleic acid from a biological sample containing a mixture of non-target nucleic acid based on the size of the nucleic acid, wherein the target nucleic acid size is less than the size of the non-target nucleic acid in the mixture, comprising the steps of introducing the biological sample to a first extraction method designed to isolate non-target nucleic acid, wherein the target nucleic acid is not substantially isolated, thereby creating a supernatant that contains target nucleic acid; removing the supernatant and introducing said supernatant to a second extraction method designed to isolate target nucleic acid, and, optionally, eluting the target nucleic acid with an elution buffer suitable for eluting nucleic acid, whereby the target nucleic acid has been selectively extracted from the sample.

In another embodiment, the present invention provides compositions, methods and kits for the adsorption of target nucleic acid to a solid support in the presence of increasing concentrations of salt, whereby the target nucleic acid is selectively enriched based on its molecular size. The compositions and methods may be used to extract and enrich the amount of normally trace nucleic acid, which is initially in the presence of high amounts of non-desired background nucleic acid, to levels suitable for detection and analysis. The invention provides compositions and methods for binding nucleic acid under specific conditions to introduce size selection with the purpose of extraction of any nucleic acid within the range of about 10 bases to about 5000 bases.

Nucleic acids are known to bind to a solid phase in the presence of a chaotropic agent (see U.S. Pat. No. 5,234,809, which is hereby incorporated by reference). Thus, provided herein are improved methods for extracting low molecular weight nucleic acid in a sample by bringing a nucleic acid-containing solution to a low salt concentration state; adsorbing the nucleic acid to a solid support and separating the solid support from the solution; bringing the solution to a high salt concentration state; adsorbing the nucleic acid to a solid support and separating the solid support from the solution; and eluting adsorbed nucleic acid from the solid support, whereby the low molecular weight nucleic acid has been selectively enriched from the sample.

In a related embodiment, the invention provides a method for extracting target nucleic acid from a biological sample containing a mixture of non-target nucleic acid based on the size of the nucleic acid, wherein the target nucleic acid size is less than the size of the non-target nucleic acid in the mixture, comprising the steps of mixing said biological sample, a salt and a nucleic acid binding solid support, wherein the salt is present at a concentration sufficient to bind non-target nucleic acid, while binding substantially little to no target nucleic acid, thereby creating a first binding solution; adsorbing the non-target nucleic acid to the solid support, and separating the solid support from the solution; removing the supernatant of the first binding solution, and mixing said supernatant with additional salt and a nucleic acid binding solid support, wherein the salt is present at a concentration sufficient to bind the target nucleic acid, thereby creating a second binding solution; adsorbing the target nucleic acid to the solid support, and separating the solid support from the second binding solution, thereby creating a solid support-target nucleic acid complex; and eluting the adsorbed target nucleic acid from the solid support with an elution buffer suitable for eluting nucleic acid, whereby the target nucleic acid has been selectively extracted from the sample.

The methods of the present invention may be used to extract nucleic acid within the range of about 10 bases to about 5000 bases. In a preferred embodiment, the target nucleic acid is at least about 25 base pairs, but less than about 1200 base pairs, and can be between about 200 base pairs and about 600 base pairs.

The present invention relates to extracting nucleic acids such as DNA, RNA, mRNA, oligonucleosomal, mitochondrial, epigenetically modified, single-stranded, double-stranded, circular, plasmid, cosmid, yeast artificial chromosomes, artificial or man-made DNA, including unique DNA sequences, and DNA that has been reverse transcribed from an RNA sample, such as cDNA, and combinations thereof. In a preferred embodiment, the nucleic acid is cell-free nucleic acid. In another embodiment, the nucleic acids are derived from apoptotic cells. In another embodiment, the target nucleic acid is of fetal origin, and the non-target nucleic acid is of maternal origin.

The present invention relates to extracting nucleic acid from a biological sample such as whole blood, serum, plasma, umbilical cord blood, chorionic villi, amniotic fluid, cerbrospinal fluid, spinal fluid, lavage fluid (e.g., bronchoalveolar, gastric, peritoneal, ductal, ear, athroscopic) biopsy sample, urine, feces, sputum, saliva, nasal mucous, prostate fluid, semen, lymphatic fluid, bile, tears, sweat, breast milk, breast fluid, embryonic cells and fetal cells. In a preferred embodiment, the biological sample is plasma. In another preferred embodiment, the biological sample is cell-free or substantially cell-free. In a related embodiment, the biological sample is a sample of previously extracted nucleic acids.

The present invention is particularly useful for extracting fetal nucleic acid from maternal plasma. In a preferred embodiment, the biological sample is from an animal, most preferably a human. In another preferred embodiment, the biological sample is from a pregnant human. In a related embodiment, the biological sample is collected from a pregnant human after the fifth week of gestation. In another embodiment, the pregnant human has a relatively elevated concentration of free fetal nucleic acid in her blood, plasma or amniotic fluid. In another embodiment, the pregnant human has a relatively decreased concentration of apoptotic nucleic acid in her blood, plasma or amniotic fluid. The methods of the present invention may be performed in conjunction with any known method to elevate fetal nucleic acid in maternal blood, plasma or amniotic fluid. Likewise, the methods of the present invention may be performed in conjunction with any known method to decrease apoptotic nucleic acid in maternal blood, plasma or amniotic fluid.

The present invention is based on the ability of nucleic acid to reversibly bind to a nucleic acid-binding solid support in the presence of a salt, such as guanidine salt, sodium iodide, potassium iodide, sodium thiocyanate, urea, sodium chloride, magnesium chloride, calcium chloride, potassium chloride, lithium chloride, barium chloride, cesium chloride, ammonium acetate, sodium acetate, ammonium perchlorate or sodium perchlorate, for example. In a preferred embodiment, the salt is a guanidine salt, most preferably guanidine (iso)thiocyanate, or is a sodium salt, most preferably sodium perchlorate. In the methods provided herein, the salt is introduced at a concentration to bind nucleic acid to a solid support. In the first binding solution, a salt is added to yield a solution with a concentration in the range of 10 to 30% weight per volume capable of binding non-target nucleic acid, while minimizing the binding of target nucleic acid. In a preferred embodiment, the non-target nucleic acid is at least 1200 base pairs. In the second binding solution, a chaotropic substance is added to yield a solution with a salt concentration greater than 10%, and preferably in the range of 20 to 60% weight per volume, which is capable of binding target nucleic acid.

In a related embodiment, the solid support is a hydroxyl donor (e.g., silica or glass) or contains a functional group that serves as a hydroxyl donor and is attached to a solid support. Examples of solid supports include paramagnetic microparticles, silica gel, silica particles, controlled pore glass, magnetic beads, biomagnetic separation beads, microspheres, divinylbenzene (DVB) resin, cellulose beads, capillaries, filter membranes, columns, nitrocellulose paper, flat supports, glass surfaces, metal surfaces, plastic materials, multiwell plates or membranes, wafers, combs, pins and needles, or any combination thereof, for example. In a preferred embodiment, the solid support is modified to reversibly bind nucleic acid. In another preferred embodiment, the solid support is a silica gel membrane.

In a related embodiment, the nucleic acid-solid support interaction is an electrostatic interaction. In another embodiment, the nucleic acid-solid support interaction is a polar interaction.

In a related embodiment, the solid support has a functional group-coated surface. In a preferred embodiment, the functional group-coated surface is silica-coated, hydroxyl coated, amine-coated, carboxyl-coated or encapsulated carboxyl group-coated, for example. A bead may be silica-coated or a membrane may contain silica gel in certain embodiments.

In the present invention, it is necessary to separate the nucleic acid-coated solid support from the first or second binding solutions. The solid support (e.g., silica-coated magnetic bead) can be separated from the solutions by any method known in the art, including applying a magnetic field, applying vacuum filtration and/or centrifugation, or any combination thereof. In a preferred embodiment, paramagnetic beads are separated from one or both solutions using magnets or magnetic devices.

The methods provided herein may also be modified to introduce additional steps, for example, in order to improve the extraction of nucleic acid or improve analysis of target nucleic acid following extraction. For example, the biological sample may be first lysed in the presence of a lysis buffer, which may comprise a chaotropic substance (e.g., salt), a proteinase, a protease or a detergent, or combinations thereof, for example. The lysis step and the creation of the first binding solution may be performed simultaneously at a salt concentration sufficient to solubilize or precipitate non-nucleic acid material (e.g., protein) in the sample and to bind the non-target nucleic acid to the solid support. In another embodiment, the method includes adding a washing step or steps to remove non-nucleic acid from the solid-support-target nucleic acid complex. In another embodiment, the solid support-target nucleic acid complex is further washed successively with a wash buffer and one or more alcohol-water solutions, and subsequently dried. In a preferred embodiment, the wash buffer comprises a chaotropic substance (e.g., salt), and optionally, a carrier such as LPA, RNA, tRNA, dextran blue, glycogen or polyA RNA, for example. In another embodiment, the second binding solution also comprises a carrier such as LPA, RNA, tRNA, dextran blue, glycogen or polyA RNA, for example.

The methods provided herein may also be modified to combine steps, for example, in order to improve automation. For example, mixing the first binding solution and adsorbing the non-target nucleic acid to the solid support may be performed simultaneously. Likewise, mixing the second binding solution and adsorbing the target nucleic acid to the solid support may be performed simultaneously.

In another embodiment, the methods provided herein may be performed prior to, subsequent to, or simultaneously with another method for extracting nucleic acid such as electrophoresis, liquid chromatography, size exclusion, microdialysis, electrodialysis, centrifugal membrane exclusion, organic or inorganic extraction, affinity chromatography, PCR, genome-wide PCR, sequence-specific PCR, methylation-specific PCR, introducing a silica membrane or molecular sieve, and fragment selective amplification.

The present invention also further relates to a kit comprising reagents for a first binding buffer formulated to comprise a suitable salt, wherein the salt is present at a concentration appropriate for binding a non-target nucleic acid characterized by a particular size, to the solid support; a second binding buffer formulated to comprise a suitable salt, wherein the salt is present at a concentration appropriate for binding a target nucleic acid characterized by a particular size, to the solid support; an aqueous solution of functional group-coated paramagnetic microparticles; and instructions for performing the target nucleic acid extraction. In another embodiment, the kit additionally comprises reagents for the formulation of a wash buffer and an elution buffer, wherein the wash buffer dissolves impurities, but not nucleic acids bound to solid support and the elution buffer is a non-salt buffered solution with a pH range between about 7.0 to 8.5.

The present invention also provides methods for a post purification process which allows enrichment of target nucleic acid by ligation-based methods followed by amplification. In one embodiment of the invention, the present invention provides a method for selectively amplifying a target nucleic acid from a biological sample containing a mixture of non-target nucleic acid, wherein the target nucleic acid is a double stranded, blunt end nucleic acid fragment with 5' phosphorylated ends, comprising the steps of a) mixing the biological sample, a 5' adapter and a 3' adapter, wherein the 3' adapter is complementary to the 5' adapter at the 3' end and thus capable of creating a double-stranded adapter complex; b) introducing a ligase to the mixture of step a) and ligating the 5' adapter of the double-stranded adapter complex to the target nucleic acid, thereby creating a ligated sample; c) heating ligated sample to release the 3' adapter; d) adding a polymerase to fill in the single-stranded 5' protruding ends; and e) adding 5' adapter primers to amplify the target nucleic acid. In a related embodiment, the method includes the additional step of performing target-specific amplification using target-specific primers. In another embodiment, a dideoxy-nucleotide is incorporated into the 3' position of the 3' adapter. In another embodiment, the 5' adapters of step a) are bound to a solid support. Optionally, spacer arms are introduced between the 5' adapter at the 5' end and the solid support. In another embodiment, solid support-bound ligation products are combined with the non-solid support products of claim 1 prior to amplification step e).

In another embodiment of the invention, a method is provided that selectively detects and amplifies target nucleic acid using a combination of the following 3 steps: 1) treating total isolated nucleic acid from a biological sample with a ligase that can covalently join blunt 5'-phosphorylated nucleic acid ends (e.g. T4 or T7 DNA ligase) under conditions that favor unimolecular circularization of the nucleic acid molecules; 2) amplifying the nucleic acid with target-specific primers and a method that is selective for circular nucleic acid, for example, either a) via a rolling circle amplification with target-specific primers, or b) via inverse PCR with target-specific primers for the gene of interest; and 3) characterizing the amplified nucleic acid by direct or indirect qualitative and/or quantitative molecular characterization methods.

DETAILED DESCRIPTION OF THE INVENTION

Figure 1:
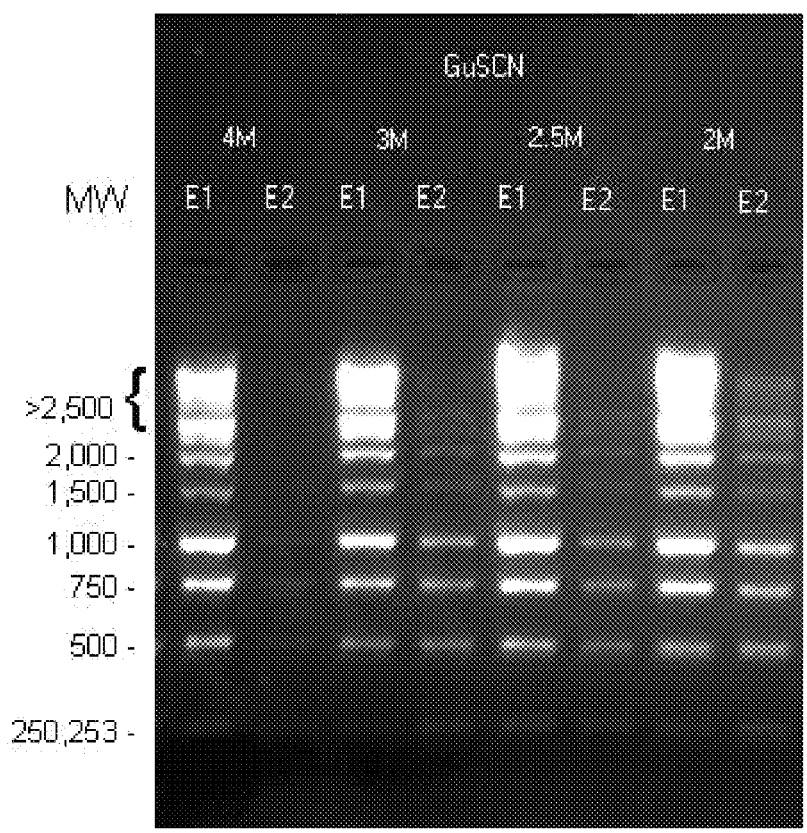
FIG. 1 shows the successful extraction of low base pair DNA from a 1 kb DNA ladder (Promega™) in the presence of guanidine thiocyanate (GuSCN).

The presence of cell-free nucleic acid in peripheral blood is a well established phenomenon. While cell-free nucleic acid may originate from several sources, it has been demonstrated that one source of circulating extracellular nucleic acid originates from programmed cell death, also known as apoptosis. The source of nucleic acid that arise as a result of apoptosis may be found in many body fluids and originate from several sources, including, but not limited to, normal programmed cell death in the host, induced programmed cell death in the case of an autoimmune disease, septic shock, neoplasms (malignant or non-malignant), or non-host sources such as an allograft (transplanted tissue), or the fetus or placenta of a pregnant woman. The applications for the detection, extraction and relative enrichment of extracellular nucleic acid from peripheral blood or other body fluids are widespread and may include inter alia, non-invasive prenatal diagnosis, cancer diagnostics, pathogen detection, autoimmune response and allograft rejection.

The present invention includes methods, compositions and kits to extract and relatively enrich by physical separation or amplification short base pair nucleic acid in the presence of a high background of genomic material (e.g., host or maternal nucleic acids). More specifically, the present invention provides compositions, methods and kits for the selective extraction and relative enrichment, based on size discrimination, of nucleic acid of approximately 1,200 base pairs or less (herein referred to as "target nucleic acid") in a high background of genomic nucleic acids (herein referred to as "non-target nucleic acid"). This leads to a relatively enriched fraction of nucleic acid that has a higher concentration of smaller nucleic acids.

The methods of the present invention may be used to improve pathogen detection. Methods for rapid identification of unknown bioagents using a combination of nucleic acid amplification and determination of base composition of informative amplicons by molecular mass analysis are disclosed and claimed in published U.S. Patent applications 20030027135, 20030082539, 20030124556, 20030175696, 20030175695, 20030175697, and 20030190605 and U.S. patent application Ser. Nos. 10/326,047, 10/660,997, 10/660,122 and 10/660,996, all of which are incorporated herein by reference in entirety.

The term "host cell" as used herein is any cell into which exogenous nucleic acid can be introduced, producing a host cell which contains exogenous nucleic acid, in addition to host cell nucleic acid. As used herein the terms "host cell nucleic acid" and "endogenous nucleic acid" refer to nucleic acid species (e.g., genomic or chromosomal nucleic acid) that are present in a host cell as the cell is obtained. As used herein, the term "exogenous" refers to nucleic acid other than host cell nucleic acid; exogenous nucleic acid can be present into a host cell as a result of being introduced in the host cell or being introduced into an ancestor of the host cell. Thus, for example, a nucleic acid species which is exogenous to a particular host cell is a nucleic acid species which is non-endogenous (not present in the host cell as it was obtained or an ancestor of the host cell). Appropriate host cells include, but are not limited to, bacterial cells, yeast cells, plant cells and mammalian cells.

The term "extraction" as used herein refers to the partial or complete separation and isolation of a nucleic acid from a biological or non-biological sample comprising other nucleic acids. The terms "selective" and "selectively" as used herein refer to the ability to extract a particular species of nucleic acid molecule, on the basis of molecular size from a combination which includes or is a mixture of species of nucleic acid molecules.

The terms "nucleic acid" and "nucleic acid molecule" may be used interchangeably throughout the disclosure. The terms refer to a deoxyribonucleotide (DNA), ribonucleotide polymer (RNA), RNA/DNA hybrids and polyamide nucleic acids (PNAs) in either single- or double-stranded form, and unless otherwise limited, would encompass known analogs of natural nucleotides that can function in a similar manner as naturally occurring nucleotides.

The term "target nucleic acid" as used herein refers to the nucleic acid of interest that is extracted based on its molecular size, preferably in a second extraction step, and further isolated for downstream analysis. In a preferred embodiment, the target nucleic acid has a molecular size smaller than the non-target nucleic acid present in the biological sample, for example, smaller than 1200 base pairs. In a related embodiment, the target nucleic acid is from apoptotic DNA, fetal DNA, oncogenic DNA, or any non-host DNA. In another related embodiment, the target nucleic acid is cell-free nucleic acid. In another related embodiment, the target nucleic acid is oligonucleosomal nucleic acid generated during programmed cell death.

The term "non-target nucleic acid" as used herein refers to the relatively high amount of non-desired background nucleic acid present in a biological sample, which is extracted, preferably, in a first extraction step. In a preferred embodiment, non-target nucleic acid has a molecular size larger than target nucleic acid, for example, greater than 1200 base pairs. In a related embodiment, non-target nucleic acid is from a host or host cell. In a preferred embodiment, non-target nucleic acid is of maternal origin.

The term "molecular size" as used herein refers to the size of a nucleic acid molecule, which may be measured in terms of a nucleic acid molecule's mass or length (bases or base pairs).

Fetal nucleic acid is present in maternal plasma from the first trimester onwards, with concentrations that increase with progressing gestational age (Lo et al. Am J Hum Genet (1998) 62:768-775). After delivery, fetal nucleic acid is cleared very rapidly from the maternal plasma (Lo et al. Am J Hum Genet (1999) 64:218-224). Fetal nucleic acid is present in maternal plasma in a much higher fractional concentration than fetal nucleic acid in the cellular fraction of maternal blood (Lo et al. Am J Hum Genet (1998) 62:768-775). Thus, in another embodiment, the target nucleic acid is of fetal origin, and the non-target nucleic acid is of maternal origin.

The present invention relates to extracting nucleic acid from a biological sample such as whole blood, serum, plasma, umbilical cord blood, chorionic villi, amniotic fluid, cerbrospinal fluid, spinal fluid, lavage fluid (e.g., broncho-alveolar, gastric, peritoneal, ductal, ear, athroscopic), biopsy sample, urine, feces, sputum, saliva, nasal mucous, prostate fluid, semen, lymphatic fluid, bile, tears, sweat, breast milk, breast fluid, embryonic cells and fetal cells. In a preferred embodiment, the biological sample is blood, and more preferably plasma. As used herein, the term "blood" encompasses whole blood or any fractions of blood, such as serum and plasma as conventionally defined. Blood plasma refers to the fraction of whole blood resulting from centrifugation of blood treated with anticoagulants. Blood serum refers to the watery portion of fluid remaining after a blood sample has coagulated. In a preferred method, blood handling protocols are followed to ensure minimal degradation of nucleic acid in the sample and to minimize the creation of apoptotic nucleic acid in the sample. Blood handling methods are well known in the art.

In another preferred embodiment, the biological sample is cell-free or substantially cell-free. In a related embodiment, the biological sample is a sample containing previously extracted, isolated or purified nucleic acids. One way of targeting target nucleic acid is to use the non-cellular fraction of a biological sample; thus limiting the amount of intact cellular material (e.g., large strand genomic DNA) from contaminating the sample. In an embodiment of the invention, a cell-free sample such as pre-cleared plasma, urine, etc. is first treated to inactivate intracellular nucleases through the addition of an enzyme, a chaotropic substance, a detergent or any combination thereof. In another embodiment, the biological sample is first treated to remove substantially all cells from the sample by any of the methods known in the art, for example, centrifugation, filtration, affinity chromatography, etc.

The term "concentration sufficient to selectively bind" as used herein refers to an amount sufficient to cause at least 50%, more preferably 70%, even more preferably 90% or more of the target nucleic acid to bind to an adsorptive surface. Suitable solid phase carriers include, but are not limited to, other particles, fibers, beads and or supports which have an affinity for nucleic acids or may be modified (e.g., the addition of a functional group or groups) to bind nucleic acids, and which can embody a variety of shapes, that are either regular or irregular in form, provided that the shape maximizes the surface area of the solid phase, and embodies a carrier which is amenable to microscale manipulations. In a preferred embodiment, silica-coated magnetic beads are used. In a preferred embodiment, the solid support is modified to reversibly bind nucleic acid. In a related embodiment, the solid support has a functional group-coated surface. In a preferred embodiment, the functional group-coated surface is silica-coated, hydroxyl-coated, amine-coated, carboxyl-coated and encapsulated carboxyl group-coated.

The term "functional group-coated surface" as used herein refers to a surface which is coated with moieties which reversibly bind nucleic acids. One example is a surface which is coated with moieties which each have a free functional group which is bound to the amino group of the amino silane or the solid support; as a result, the surfaces of the solid support are coated with the functional group containing moieties. In one embodiment, the functional group is a carboxylic acid. A suitable moiety with a free carboxylic acid functional group is a succinic acid moiety in which one of the carboxylic acid groups is bonded to the amine of amino silanes through an amide bond and the second carboxylic acid is unbonded, resulting in a free carboxylic acid group attached or tethered to the surface of the paramagnetic microparticle. Suitable solid phase carriers having a functional group coated surface that reversibly binds nucleic acid molecules are for example, magnetically responsive solid phase carriers having a functional group-coated surface, such as, but not limited to, silica-coated, hydroxyl-coated, amino-coated, carboxyl-coated and encapsulated carboxyl group-coated magnetic beads. In another example, an oligonucleotide of the invention (e.g., an adapter or primer) is labeled with biotin which may bind to immobilized streptavidin.

The extraction of nucleic acid from biological material requires cell lysis, inactivation of cellular nucleases and separation of the desired nucleic acid from cellular debris. Common lysis procedures include mechanical disruption (e.g., grinding, hypotonic lysis), chemical treatment (e.g., detergent lysis, chaotropic agents, thiol reduction), and enzymatic digestion (e.g., proteinase K). In the present invention, the biological sample may be first lysed in the presence of a lysis buffer, chaotropic agent (e.g., salt) and proteinase or protease. Cell membrane disruption and inactivation of intracellular nucleases may be combined. For instance, a single solution may contain detergents to solubilise cell membranes and strong chaotropic salts to inactivate intracellular enzymes. After cell lysis and nuclease inactivation, cellular debris may easily be removed by filtration or precipitation.

In another embodiment, lysis may be blocked. In these embodiments, the sample may be mixed with an agent that inhibits cell lysis to inhibit the lysis of cells, if cells are present, where the agent is a membrane stabilizer, a cross-linker, or a cell lysis inhibitor. In some of these embodiments, the agent is a cell lysis inhibitor, and may be glutaraldehyde, derivatives of glutaraldehyde, formaldehyde, formalin, or derivatives of formaldehyde. See U.S. patent application 20040137470, which is hereby incorporated by reference.

In another embodiment, the method includes adding a washing step or steps to remove non-nucleic acid molecules, for example salts, from the solid-support-target nucleic acid complex or surrounding solution. Non-nucleic acid molecules are then removed with an alcohol-based wash and the target nucleic acid is eluted under low- or no-salt conditions (TE buffer or water) in small volumes, ready for immediate use without further concentration. In another embodiment, extraction is improved by the introduction of a carrier such as tRNA, glycogen, polyA RNA, dextran blue, linear poly acrylamide (LPA), or any material that increases the recovery of nucleic acid. The carriers may be added to the second binding solution or washing buffer.

In another embodiment of the invention, the final relative percentage of target nucleic acid to non-target nucleic acid is at least about 5-6% fetal DNA, about 7-8% fetal DNA, about 9-10% fetal DNA, about 11-12% fetal DNA, about 13-14% fetal DNA. about 15-16% fetal DNA, about 16-17% fetal DNA, about 17-18% fetal DNA, about 18-19% fetal DNA, about 19-20% fetal DNA, about 20-21% fetal DNA, about 21-22% fetal DNA, about 22-23% fetal DNA, about 23-24% fetal DNA, about 24-25% fetal DNA, about 25-35% fetal DNA, about 35-45% fetal DNA, about 45-55% fetal DNA, about 55-65% fetal DNA, about 65-75% fetal DNA, about 75-85% fetal DNA, about 85-90% fetal DNA, about 90-91% fetal DNA, about 91-92% fetal DNA, about 92-93% fetal DNA, about 93-94% fetal DNA, about 94-95% fetal DNA, about 95-96% fetal DNA, about 96-97% fetal DNA, about 97-98% fetal DNA, about 98-99% fetal DNA, or about 99-99.7% fetal DNA.

The methods provided herein may also be modified to combine steps, for example, in order to improve automation.

In another example, the methods of the present invention may be used in conjunction with any known technique suitable for the extraction, isolation or purification of nucleic acids, including, but not limited to, cesium chloride gradients, gradients, sucrose gradients, glucose gradients, centrifugation protocols, boiling, Microcon 100 filter, Chemagen viral DNA/RNA 1k kit, Chemagen blood kit, Qiagen purification systems, Qiagen MinElute kits, QIA DNA blood purification kit, HiSpeed Plasmid Maxi Kit, QIAfilter plasmid kit, Promega DNA purification systems, MangeSil Paramagnetic Particle based systems, Wizard SV technology, Wizard Genomic DNA purification kit, Amersham purification systems, GFX Genomic Blood DNA purification kit, Invitrogen Life Technologies Purification Systems, CONCERT purification system, Mo Bio Laboratories purification systems, UltraClean BloodSpin Kits, and UlraClean Blood DNA Kit.

In an embodiment of the invention, the first extraction method is any known or modified technique suitable for the extraction, isolation or purification of non-target nucleic acids (i.e., larger than target nucleic acids), including, but not limited to, cesium chloride gradients, gradients, sucrose gradients, glucose gradients, centrifugation protocols, boiling, Microcon 100 filter, Chemagen viral DNA/RNA 1k kit, Chemagen blood kit, Qiagen purification systems, Qiagen MinElute kits, QIA DNA blood purification kit, HiSpeed Plasmid Maxi Kit, QIAfilter plasmid kit, Promega DNA purification systems, MangeSil Paramagnetic Particle based systems, Wizard SV technology, Wizard Genomic DNA purification kit, Amersham purification systems, GFX Genomic Blood DNA purification kit, Invitrogen Life Technologies Purification Systems, CONCERT purification system, Mo Bio Laboratories purification systems, UltraClean BloodSpin Kits, and UlraClean Blood DNA Kit. In a related embodiment, one or more of the above methods is modified to selectively extract larger, non-target nucleic acids while not extracting smaller, target nucleic acids. For example, the temperature, pH or reagent concentrations of one or more of the above methods may be modified.

In another embodiment, the second extraction method is any known or modified technique suitable for the extraction, isolation or purification of target nucleic acids (i.e., smaller than non-target nucleic acids), including, but not limited to, cesium chloride gradients, gradients, sucrose gradients, glucose gradients, centrifugation protocols, boiling, Microcon 100 filter, Chemagen viral DNA/RNA 1k kit, Chemagen blood kit, Qiagen purification systems, Qiagen MinElute kits, QIA DNA blood purification kit, HiSpeed Plasmid Maxi Kit, QIAfilter plasmid kit, Promega DNA purification systems, MangeSil Paramagnetic Particle based systems, Wizard SV technology, Wizard Genomic DNA purification kit, Amersham purification systems, GFX Genomic Blood DNA purification kit, Invitrogen Life Technologies Purification Systems, CONCERT purification system, Mo Bio Laboratories purification systems, UltraClean BloodSpin Kits, and UlraClean Blood DNA Kit. In a related embodiment, one or more of the above methods is modified to selectively extract smaller nucleic acids, for example, present in a supernatant from a previously extracted sample. For example, the temperature, pH or reagent concentrations of one or more of the above methods may be modified.

The present invention also further relates to kits for practicing the methods of the invention.

Ligation-Based Methods for Selective Nucleic Acid Detection and Amplification

Programmed cell death or apoptosis is an essential mechanism in morphogenesis, development, differentiation, and homeostasis in all multicellular organisms. Typically, apoptosis is distinguished from necrosis by activation of specific pathways that result in characteristic morphological features including DNA fragmentation, chromatin condensation, cytoplasmic and nuclear breakdown, and the formation of apoptotic bodies.

Caspase-activated DNase (CAD), alternatively called DNA fragmentation factor (DFF or DFF40), has been shown to generate double-stranded DNA breaks in the internucleosomal linker regions of chromatin leading to nucleosomal ladders consisting of DNA oligomers of approximately 180 base pairs or multiples thereof. The majority of the ladder fragments (up to 70%) occur as nucleosomal monomers of 180 bp. All fragments carry 5'-phosphorylated ends and the majority of them are blunt-ended (Widlak et al, J Biol Chem. 2000 Mar. 17; 275(11):8226-32, which is hereby incorporated by reference). Since non-apoptotic DNA is lacking this feature, any method that can select for DNA fragments with blunt, 5'-phosphorylated ends, is suitable to select for specific features (such as size, sequence and DNA base methylation differences) of the apoptotic DNA in a given biological sample. See for example, US patent applications 20050019769, 20050164241, 20030044388, or 20060019278, all of which are hereby incorporated by reference.

Very short, single base 3' and 5'-overhangs have also been detected but represent a minority of the DNA species in apoptotic ladders (Didenko et al, Am J Pathol. 2003 May; 162(5):1571-8; Widlak et al, 2000, both of which are hereby incorporated by reference). Hence, methods that are selective for both, blunt, and 5'-phosphorylated blunt ends, are only slightly less sensitive but retain very high specificity for DNA of apoptotic origin.

For enrichment and detection of apoptotic DNA ladders in mammalian tissues, a method has been described that takes advantage of the presence of blunt, 5'-phosphorylated ends in apoptotic DNA by ligation of synthetic, blunt-ended linkers to both ends of linear apoptotic DNA fragments with T4 ligase which is able to form a covalent bond between the 3'-hydroxy ends of the synthetic linker and the 5'-phosphorylated ends of the DNA fragments (Staley et al, Cell Death Differ. 1997 January; 4(1):66-75, which is hereby incorporated by reference). The method can only be used as a generic tool to characterize the size distribution of apoptotic ladders in specific tissues in general, and is not site or sequence specific.

A variation of the method, that employs biotinylated hairpin probes stained with fluorescence dye streptavidin conjugates had been introduced described patent (Didenko et al 1999; U.S. Pat. Nos. 6,013,438 and 6,596,480, which are hereby incorporated by reference) to selectively detect terminal apoptotic activities in tissue sections.

Recently, the concept of blunt-end ligation-mediated whole genome amplification of apoptotic and necrotic plasma DNA has been introduced (Li et al, J Mol Diagn. 2006 February; 8(1):22-30, which is hereby incorporated by reference) for the analysis of allelic imbalance in tumor-specific DNA biomarkers. In this approach, isolated plasma DNA is first treated with T4 DNA polymerase to convert DNA fragments to blunt-ends before the blunt, 5'-phosphorylated DNA termini are self-ligated or cross ligated. The self-ligated, circular fragments are then amplified approximately 1,000 fold via random primer-initiated multiple displacement amplification. However, since this approach amplifies all apoptotic DNA sequences present in the sample, at least 1 ng (which represents about 300 genome equivalents of human DNA) is required to maintain equal genomic representation and gene-dosage and allelic ratios present before amplification.

Thus, there is an increasing need to characterize known mutations and epimutations of specific DNA fragments from specific cells or tissues or present as extracellular fragments in biological fluids in a target-specific manner in the presence of high background of wild-type DNA (e.g. somatic mutations of DNA from cells responding to a xenobiotic of drug treatment; from inflamed, malignant or otherwise diseased tissues; from transplants or from differences of fetal and maternal DNA during pregnancy).

The present invention, therefore, provides a method for selectively amplifying short, fragmented nucleic acid by adapter mediated ligation and other related methods. The method capitalizes on the blunt end and 5'-phosphorylated nature of the target nucleic acid as a means to attach a non-genome specific adapter to the blunt ends using a ligation process. While the nature of the termini of all cell-free nucleic acid is unknown, coupling this method with short extension times during amplification will favor the amplification of the oligonucleosome monomer and short multimers. Since the target nucleic acid is shorter than the non-targeted nucleic acid, the target nucleic acid can be enriched over the non-target nucleic acid. This method can be further coupled with specific amplification of a nucleic acid region of interest for further analysis. In the present invention, the 3' and 5' dephosphorylated adapters are complementary and form a double-stranded blunt end adapter complex. The 5' adapter of the adapter complex ligates to the 5' phosphorylated strand of the target nucleic acid, and heat is introduced to release the shorter, unligated 3' adapter. Next, the 5' protruding ends of the ligated complex are filled in by a thermostable DNA polymerase. The 5' adapter is reintroduced and serves as a PCR primer for whole genome amplification.

The method is particularly useful for detecting oligonucleosomes. Oligonucleosomes are the repeating structural units of chromatin, each consisting of approximately 200 base pairs of DNA wound around a histone core that partially protects the DNA from nuclease digestion in vitro and in vivo. These units can be found as monomers or multimers and produce what is commonly referred to as an apoptotic DNA ladder. The units are formed by nuclease digestion of the flanking DNA not bound to histone resulting in the majority of oligonucleosomes being blunt ended and 5'-phosphorylated. In biological systems in which only a small percentage of cells are apoptotic, or in which apoptosis is occurring asynchronously, oligonucleosomes are hard to detect and harder to isolate; however, they can serve as predictors for disease and other conditions (see US patent application 20040009518, which is hereby incorporated by reference).

The term "5' dephosphorylated adapter" as used herein refers to a nucleic acid which comprises about 20 to 30 base pairs that is complementary to a short dephosphorylated adapter and capable of hybridizing thereto to form a double-stranded, blunt end adapter complex capable of ligating to target nucleic acid. Specifically, the 5'adapter ligates to the 5'phosphorylated base of the target nucleic acid.

The term "3' dephosphorylated adapter" refers to a nucleic acid which comprises about 10 to 15 base pairs that is complementary to the 5' adapter at the 3' end, thus capable of creating a double-stranded blunted end necessary for ligation. The 3' adapter does not bind or ligate to the oligonucleosomal DNA.

The term "5' adapter primer" as used herein refers to the same oligonucleotide sequence as the 5' dephosphorylated adapter, but is later reintroduced to the ligated sample to facilitate the whole genome amplification.

The term "adapter complex" as used herein refers to the hybridized, double-stranded 5' adapter and 3' adapter molecule.

The method is semi quantitative. By comparing the numbers of PCR cycles needed to detect target nucleic acid in two samples, the relative amount of target nucleic acid occurring in each sample can be estimated.

In another embodiment of the invention, the 5' adapters are bound to a solid support for increased enrichment of the target nucleic acid. In this embodiment, non-ligated, non-target nucleic acid is substantially removed from the solution, and amplification can proceed using only the targeted material that has ligated to the 5' adapters. This embodiment of the invention improves the enrichment of the target nucleic acid by removing genomic non-target nucleic acid that may compete with the target nucleic acid in the target-specific amplification step. For example, in a maternal sample, if the target sequence is present in both the mother and the fetus, and the maternal sample is very abundant (>95%), under normal circumstances the fetal nucleic acid would not be detectable as it would be out-competed by the maternal nucleic acid in the first cycles of amplification. If the fetal nucleic acid is part or wholly oligonucleosomal in nature, and the majority of the ligated sample is fetal in nature, maternal nucleic acid is still present in the sample, which can compete with the fetal nucleic acid in the target-specific amplification step. Separation of non-target nucleic acid from the target nucleic acid (i.e., ligated sample) increases the detection of fetal nucleic acid in cases where there is an abundance of maternal nucleic acid in the initial biological sample, there is sample degradation, or there is a maternal condition (e.g., autoimmune disease, transplant rejection, cancer) that increases the amount of maternal oligonucleosomes. In a related embodiment, spacer arms are introduced between the solid support and 5' adapter to improve ligation of the target nucleic acid to the adapter molecule. In another related embodiment, the ligated sample bound to a solid support is combined with a ligated sample that does not have a solid support prior to the amplification step.

The term "spacer arms" as used herein refers to any molecule that can be used in single or multiples to create space between the solid support and an oligonucleotide (e.g., target nucleic acid). In a preferred embodiment of the invention, one or more hexaethylene (HEG) spacer units are inserted between the aminohexyl groups and the 5' end of the 5' adapter. The aminohexyl group is used for covalent coupling to the solid support. Other examples of spacer arms that may be used in the present invention include multiple dTTP's (up to 15), spacer 18 (an 18 atom hexa-ethylene glycol spacer), spacer 9 (a triethylene glycol spacer), or photocleavable spacers known in the art.

An alternative method of the present invention selectively detects and amplifies target nucleic acid using a combination of the following 3 steps:

1) treating total isolated DNA from a biological sample with a ligase that can covalently join blunt 5'-phosphorylated DNA ends (e.g. T4 or T7 DNA ligase) under conditions that favor unimolecular circularization of the DNA molecules;

2) amplifying the DNA with target-specific primers and a method that is selective for circular DNA, for example, either a) via a rolling circle amplification with target-specific primers, or b) via inverse PCR with target-specific primers for the gene of interest; and 3) characterizing the amplified DNA by direct or indirect qualitative and/or quantitative molecular characterization methods, such as: a) Sequenom Inc.'s primer extension method (e.g., iPLEX™), orb) any known method for detection and quantitation of nucleic acids such as DNA sequencing, restriction fragment length polymorphism (RFLP analysis), allele specific oligonucleotide (ASO) analysis, methylation-specific PCR (MSPCR), pyrosequencing analysis, acycloprime analysis, Reverse dot blot, GeneChip microarrays, Dynamic allele-specific hybridization (DASH), Peptide nucleic acid (PNA) and locked nucleic acids (LNA) probes, TaqMan, Molecular Beacons, Intercalating dye, FRET primers, AlphaScreen, SNPstream, genetic bit analysis (GBA), Multiplex minisequencing, SNaPshot, GOOD assay, Microarray miniseq, arrayed primer extension (APEX), Microarray primer extension, Tag arrays, Coded microspheres, Template-directed incorporation (TDI), fluorescence polarization, Colorimetric oligonucleotide ligation assay (OLA), Sequence-coded OLA, Microarray ligation, Ligase chain reaction, Padlock probes, and Invader assay, or combinations thereof.

Any combination of these 3 steps will selectively enrich the double-stranded, blunt-ended 5'-phosphorylated DNA such as DNA from apoptotic ladders by several orders of magnitude over the DNA fragments present in the biological sample that cannot by circularized due to lack of blunt ends and/or missing 5'-terminal phosphate groups and allow a comparison of its sequence with the wild-type sequence of the same organism or the host organism in case of a transplant or a maternal sequence in case of a pregnancy, for instance.

In a variation of the method, before step 2, an aliquot of the total DNA is either treated with methylation-sensitive or methylation-resistant enzymes or with chemicals that convert methylated bases into different bases so that methylated bases in the apoptotic DNA fragments can be characterized after step 2 and 3.

Diagnostic Applications

Circulating nucleic acids in the plasma and serum of patients are associated with certain diseases and conditions (See, Lo Y M D et al., N Eng J Med 1998; 339:1734-8; Chen X Q, et al., Nat Med 1996; 2:1033-5, Nawroz H et al., Nat Med 1996; 2:1035-7; Lo Y M D et al., Lancet 1998; 351:1329-30; Lo Y M D, et al., Clin Chem 2000; 46:319-23). Further, the method of nucleic acid isolation may affect the ability to detect these disease-associated nucleic acids circulating in the blood (Wang et al. Clin Chem. 2004 January; 50(1):211-3).

The characteristics and biological origin of circulating nucleic acids are not completely understood. However, it is likely that cell death, including apoptosis, is one major factor (Fournie e al., Gerontology 1993; 39:215-21; Fournie et al., Cancer Lett 1995; 91:221-7). Without being bound by theory, as cells undergoing apoptosis dispose nucleic acids into apoptotic bodies, it is possible that at least part of the circulating nucleic acids in the plasma or serum of human subjects is short, fragmented DNA that takes the form particle-associated nucleosomes. The present invention provides methods for extracting the short, fragmented circulating nucleic acids present in the plasma or serum of subjects, thereby enriching the short, predictive nucleic acids relative to the background genomic DNA.

The present invention provides methods of evaluating a disease condition in a patient suspected of suffering or known to suffer from the disease condition. In one embodiment of the present invention, the invention includes obtaining a biological sample from the patient suspected of suffering or known to suffer from a disease condition, selectively extracting and enriching extracellular nucleic acid in the sample based on its size using the methods provided herein, and evaluating the disease condition by determining the amount or concentration or characteristic of enriched extracellular nucleic acid and comparing the amount or concentration or characteristic of enriched extracellular nucleic acid to a control (e.g., background genomic DNA from biological sample).

The phrase "evaluating a disease condition" refers to assessing the disease condition of a patient. For example, evaluating the condition of a patient can include detecting the presence or absence of the disease in the patient. Once the presence of disease in the patient is detected, evaluating the disease condition of the patient may include determining the severity of disease in the patient. It may further include using that determination to make a disease prognosis, e.g. a prognosis or treatment plan. Evaluating the condition of a patient may also include determining if a patient has a disease or has suffered from a disease condition in the past. Evaluating the disease condition in that instant might also include determining the probability of reoccurrence of the disease condition or monitoring the reoccurrence in a patient. Evaluating the disease condition might also include monitoring a patient for signs of disease. Evaluating a disease condition therefore includes detecting, diagnosing, or monitoring a disease condition in a patient as well as determining a patient prognosis or treatment plan. The method of evaluating a disease condition aids in risk stratification.

Cancer

The methods provided herein may be used to extract oncogenic nucleic acid, which may be further used for the detection, diagnosis or prognosis of a cancer-related disorder. In plasma from cancer patients, nucleic acids, including DNA and RNA, are known to be present (Lo K W, et al. *Clin Chem* (1999) 45, 1292-1294). These molecules are likely packaged in apoptotic bodies and, hence, rendered more stable compared to 'free RNA' (Anker P and Stroun M, *Clin Chem* (2002) 48, 1210-1211; Ng E K, et al. *Proc Natl Acad Sci USA* (2003) 100, 4748-4753).

In the late 1980s and 1990s several groups demonstrated that plasma DNA derived from cancer patients displayed tumor-specific characteristics, including decreased strand stability, Ras and p53 mutations, microsatellite alterations, abnormal promoter hypermethylation of selected genes, mitochondrial DNA mutations and tumor-related viral DNA (Stroun M, et al. *Oncology* (1989) 46, 318-322; Chen X Q, et al. *Nat Med* (1996) 2, 1033-1035; Anker P, et al. *Cancer Metastasis Rev* (1999) 18, 65-73; Chan K C and Lo Y M, *Histol Histopathol* (2002) 17, 937-943). Tumor-specific DNA for a wide range of malignancies has been found: haematological, colorectal, pancreatic, skin, head-and-neck, lung, breast, kidney, ovarian, nasopharyngeal, liver, bladder, gastric, prostate and cervix. In aggregate, the above data show that tumor-derived DNA in plasma is ubiquitous in affected patients, and likely the result of a common biological process such as apoptosis. Investigations into the size of these plasma DNA fragments from cancer patients has revealed that the majority show lengths in multiples of nucleosomal DNA, a characteristic of apoptotic DNA fragmentation (Jahr S, et al. *Cancer Res* (2001) 61, 1659-1665).

If a cancer shows specific viral DNA sequences or tumor suppressor and/or oncogene mutant sequences, PCR-specific strategies can be developed. However, for most cancers (and most Mendelian disorders), clinical application awaits optimization of methods to isolate, quantify and characterize the tumor-specific DNA compared to the patient's normal DNA, which is also present in plasma. Therefore, understanding the molecular structure and dynamics of DNA in plasma of normal individuals is necessary to achieve further advancement in this field.

Thus, the present invention relates to detection of specific extracellular nucleic acid in plasma or serum fractions of human or animal blood associated with neoplastic, premalignant or proliferative disease. Specifically, the invention relates to detection of nucleic acid derived from mutant oncogenes or other tumor-associated DNA, and to those methods of detecting and monitoring extracellular mutant oncogenes or tumor-associated DNA found in the plasma or serum fraction of blood by using DNA extraction with enrichment for mutant DNA as provided herein. In particular, the invention relates to the detection, identification, or monitoring of the existence, progression or clinical status of benign, premalignant, or malignant neoplasms in humans or other animals that contain a mutation that is associated with the neoplasm through the size selective enrichment methods provided herein, and subsequent detection of the mutated nucleic acid of the neoplasm in the enriched DNA.

The present invention features methods for identifying DNA originating from a tumor in a biological sample. These methods may be used to differentiate or detect tumor-derived DNA in the form of apoptotic bodies or nucleosomes in a biological sample. In preferred embodiments, the non-cancerous DNA and tumor-derived DNA are differentiated by observing nucleic acid size differences, wherein low base pair DNA is associated with cancer.

Prenatal Diagnostics

Since 1997, it is known that free fetal DNA can be detected in the blood circulation of pregnant women. In absence of pregnancy-associated complications, the total concentration of circulating DNA is in the range of 10-100 ng or 1,000 to 10,000 genome equivalents/ml plasma (Bischoff et al., Hum Reprod Update. 2005 January-February; 11(1):59-67 and references cited therein) while the concentrations of the fetal DNA fraction increases from ca. 20 copies/ml in the first trimester to >250 copies/ml in the third trimester. After electron microscopic investigation and ultrafiltration enrichment experiments, the authors conclude that apoptotic bodies carrying fragmented nucleosomal DNA of placental origin are the source of fetal DNA in maternal plasma.

It has been demonstrated that the circulating DNA molecules are significantly larger in size in pregnant women than in non-pregnant women with median percentages of total plasma DNA of >201 bp at 57% and 14% for pregnant and non-pregnant women, respectively while the median percentages of fetal-derived DNA with sizes >193 bp and >313 bp were only 20% and 0%, respectively (Chan et al, Clin Chem. 2004 January; 50(1):88-92).

These findings have been independently confirmed (Li et al, Clin Chem. 2004 June; 50(6):1002-11); Patent application US200516424, which is hereby incorporated by reference) who showed as a proof of concept, that a >5 fold relative enrichment of fetal DNA from ca. 5% to >28% of total circulating plasma DNA is possible be means of size exclusion chromatography via preparative agarose gel electrophoresis and elution of the <300 bp size fraction. Unfortunately, the method is not very practical for reliable routine use because it is difficult to automate and due to possible loss of DNA material and the low concentration of the DNA recovered from the relevant Agarose gel section.

Thus, the present invention features methods for differentiating DNA species originating from different individuals in a biological sample. These methods may be used to differentiate or detect fetal DNA in a maternal sample. In preferred embodiments, the DNA species are differentiated by observing nucleic acid size differences.

The differentiation between maternal and fetal DNA may be performed with or without quantifying the concentration of fetal DNA in maternal plasma or serum. In embodiments wherein the fetal DNA is quantified, the measured concentration may be used to predict, monitor or diagnose or prognosticate a pregnancy-associated disorder.

There are a variety of non-invasive and invasive techniques available for prenatal diagnosis including ultrasonography, amniocentesis, chorionic villi sampling (CVS), fetal blood cells in maternal blood, maternal serum alpha-fetoprotein, maternal serum beta-HCG, and maternal serum estriol. However, the techniques that are non-invasive are less specific, and the techniques with high specificity and high sensitivity are highly invasive. Furthermore, most techniques can be applied only during specific time periods during pregnancy for greatest utility The first marker that was developed for fetal DNA detection in maternal plasma was the Y chromosome, which is present in male fetuses (Lo et al. *Am J Hum Genet* (1998) 62:768-775). The robustness of Y chromosomal markers has been reproduced by many workers in the field (Costa J M, et al. *Prenat Diagn* 21:1070-1074). This approach constitutes a highly accurate method for the determination of fetal gender, which is useful for the prenatal investigation of sex-linked diseases (Costa J M, Ernault P (2002) *Clin Chem* 48:679-680).

Maternal plasma DNA analysis is also useful for the noninvasive prenatal determination of fetal RhD blood group status in RhD-negative pregnant women (Lo et al. (1998) *N Engl J Med* 339:1734-1738). This approach has been shown by many groups to be accurate, and has been introduced as a routine service by the British National Blood Service since 2001 (Finning K M, et al. (2002) *Transfusion* 42:1079-1085).

More recently, maternal plasma DNA analysis has been shown to be useful for the noninvasive prenatal exclusion of fetal β-thalassemia major (Chiu R W K, et al. (2002) *Lancet* 360:998-1000). A similar approach has also been used for prenatal detection of the HbE gene (Fucharoen G, et al. (2003) *Prenat Diagn* 23:393-396).

Other genetic applications of fetal DNA in maternal plasma include the detection of achondroplasia (Saito H, et al. (2000) *Lancet* 356:1170), myotonic dystrophy (Amicucci P, et al. (2000) *Clin Chem* 46:301-302), cystic fibrosis (Gonzalez-Gonzalez M C, et al. (2002) *Prenat Diagn* 22:946-948), Huntington disease (Gonzalez-Gonzalez M C, et al. (2003) *Prenat Diagn* 23:232-234), and congenital adrenal hyperplasia (Rijnders R J, et al. (2001) *Obstet Gynecol* 98:374-378). It is expected that the spectrum of such applications will increase over the next few years.

In another aspect of the present invention, the patient is pregnant and the method of evaluating a disease or physiological condition in the patient or her fetus aids in the detection, monitoring, prognosis or treatment of the patient or her fetus. More specifically, the present invention features methods of detecting abnormalities in a fetus by detecting fetal DNA in a biological sample obtained from a mother. The methods according to the present invention provide for detecting fetal DNA in a maternal sample by differentiating the fetal DNA from the maternal DNA based on DNA characteristics (e.g., size, weight, 5' phosphorylated, blunt end). See Chan et al. *Clin Chem.* 2004 January; 50(1):88-92; and Li et al. Clin Chem. 2004 June; 50(6):1002-11. Employing such methods, fetal DNA that is predictive of a genetic anomaly or genetic-based disease may be identified thereby providing methods for prenatal diagnosis. These methods are applicable to any and all pregnancy-associated conditions for which nucleic acid changes, mutations or other characteristics (e.g., methylation state) are associated with a disease state. Exemplary diseases that may be diagnosed include, for example, preeclampsia, preterm labor, hyperemesis gravidarum, ectopic pregnancy, fetal chromosomal aneuploidy (such as trisomy 18, 21, or 13), and intrauterine growth retardation.

The compositions, methods and kits of the present invention allow for the analysis of fetal genetic traits including those involved in chromosomal aberrations (e.g. aneuploidies or chromosomal aberrations associated with Down's syndrome) or hereditary Mendelian genetic disorders and, respectively, genetic markers associated therewith (e.g. single gene disorders such as cystic fibrosis or the hemoglobinopathies). Size-based extraction of extracellular fetal DNA in the maternal circulation thus facilitates the non-invasive detection of fetal genetic traits, including paternally inherited polymorphisms which permit paternity testing.

The term "pregnancy-associated disorder," as used in this application, refers to any condition or disease that may affect a pregnant woman, the fetus the woman is carrying, or both the woman and the fetus. Such a condition or disease may manifest its symptoms during a limited time period, e.g., during pregnancy or delivery, or may last the entire life span of the fetus following its birth. Some examples of a pregnancy-associated disorder include ectopic pregnancy, preeclampsia, preterm labor, and fetal chromosomal abnormalities such as trisomy 13, 18, or 21.

The term "chromosomal abnormality" refers to a deviation between the structure of the subject chromosome and a normal homologous chromosome. The term "normal" refers to the predominate karyotype or banding pattern found in healthy individuals of a particular species. A chromosomal abnormality can be numerical or structural, and includes but is not limited to aneuploidy, polyploidy, inversion, a trisomy, a monosomy, duplication, deletion, deletion of a part of a chromosome, addition, addition of a part of chromosome, insertion, a fragment of a chromosome, a region of a chromosome, chromosomal rearrangement, and translocation. A chromosomal abnormality can be correlated with presence of a pathological condition or with a predisposition to develop a pathological condition.

Other Diseases

Many diseases, disorders and conditions (e.g., tissue or organ rejection) produce apoptotic or nucleosomal DNA that may be detected by the methods provided herein. Diseases and disorders believed to produce apoptotic DNA include diabetes, heart disease, stroke, trauma and rheumatoid arthritis. Lupus erythematosus (SLE) (Rumore and Steinman J Clin Invest. 1990 July; 86(1):69-74). Rumore et al. noted that DNA purified from SLE plasma formed discrete bands, corresponding to sizes of about 150-200, 400, 600, and 800 bp, closely resembling the characteristic 200 bp "ladder" found with oligonucleosomal DNA.

The present invention also provides a method of evaluating the disease condition of a patient suspected of having suffered from a trauma or known to have suffered from a trauma. The method includes obtaining a sample of plasma or serum from the patient suspected of having suffered from a trauma or known to have had suffered from a trauma, and detecting the quantity or concentration of mitochondrial nucleic acid in the sample.

EXAMPLES

The examples hereafter illustrate but do not limit the invention.

Example 1

Isolation of DNA Using a Double Extraction Salt-Based Method

The example provides a procedure, using a method provided herein, to selectively extract DNA based on its size.

1. Protein Denaturation and Protein Digestion

Add a low concentration of chaotropic salt, for example, less than 30% solution (weight per volume) to the sample solution to denature proteins and inactivate nucleases, proteinase K or any protease, for example 100 to 1000 µg) to further inactivate nucleases and break down proteins in solution. Alternatively, detergents, for example SDS or Triton-X 100 up to 1% volume per volume, may be used alone or in combination with a salt.

Mix the solution thoroughly, and incubate for 10-30 minutes at 55° C., or sufficient time and temperature for the enzyme in use.

2. Binding of Non-Target Nucleic Acid

Add a low concentration of salt, for example, 10-30% weight per volume, and add the solid support.

Mix the solution thoroughly, and incubate 10-30 minutes at ambient temperature.

3. Separate of the Solid Support from the Solution

Transfer the solid support or solution from the vessel to a new vessel.

4. Binding of Target Nucleic Acid

Add a high concentration of salt, for example, 20-60% weight per volume, and add (fresh) solid support.

Add a Carrier Complex.

Mix the solution thoroughly, and incubate 10-30 minutes at ambient temperature.

5. Separate the Solid Support from the Solution

Discard the supernatant and proceed to washing the target nucleic acid-bound solid support.

6. Washing

Wash target nucleic acid-bound solid support using an appropriate washing solution comprised of salt, buffer, water and alcohol. (Addition of carrier to wash solution may increase recovery).

Remove washing solution and repeat by gradually increasing alcohol concentration in the wash solution.

7. Air Dry

Air dry solid support at ambient temperature or by exposing to heat to completely dry and remove any remaining alcohol that would inhibit downstream use of the sample.

8. Elution

Release the target nucleic acid from the solid support by addition of sufficient sterile water or buffered solution (e.g. 1×TE pH 7-8.5) at ambient temperature or by exposing to heat.

9. Collect Elute Containing Targeted Nucleic Acid.

Example 2

DNA Extraction in the Presence of Guanidine Thiocyanate (GuSCN)

FIG. 1 shows the successful extraction of low base pair DNA from a 1 kb DNA ladder (Promega™) in the presence of guanidine thiocyanate (GuSCN). The DNA is first bound to silica at various low concentrations of guanidine thiocyanate as shown in FIG. 1. The supernatant from the first binding solution is subsequently bound to silica at varying guanidine thiocyanate concentrations, with a finishing high concentration of 4.6M. These steps are followed by wash and elution steps.

The method can be employed to produce size selective separation of a commercially available DNA ladder with DNA strands ranging in mass from 250 bp to 10,000 bp from normal human plasma in the presence of guanidine thiocyanate as the chaotropic salt. The following steps are performed:

1. To four separate vessels, add 10 µL protease solution (20 ug/µL), 200 µL normal human plasma, and 100 µL 4.5 M GuSCN (final concentration 1.45 M).
2. Add GuSCN sufficient to increase the concentration to 4M, 3M, 2.5M or 2M. Add 5 µL hydrated silica, 10 µL 1 kb ladder. Mix the solution and incubated 10 minutes at ambient temperature.
3. Centrifuge at 7,000 rpm for 2.5 minutes. Transfer the supernatant to a new vessel. Label the non-target DNA silica as E1 and proceed to washing step (Step 6).
4. Increase the concentration of the supernatant to 4.6 M GuSCN for all samples. Add 5 µL of silica, mix and incubate for 10 minutes at ambient temperature.
5. Centrifuge at 7,000 rpm for 2.5 minutes. Discard the supernatant. Label the target DNA silica as E2 and proceed to washing step (Step 6).
6. Wash pellet 1×500 µL of 2 M GuSCN in 67% ethanol, 1×500 µL of 1M GuSCN in 83% ethanol, 1×100 µl ethanol.
7. Air dry silica 5 minutes on low heat.
8. Add 10 µL of 1×TE and incubate at 55 degrees C. for 10 minutes.
9. Transfer eluates for E1 and E2 to new tube. Add 2.5 µL bromophenol blue loading buffer, and load 10 µL per lane onto a 1.2% agarose gel in 1×TBE. Electrophoresis is used to separate the DNA strands, and ethidium bromide is used to visualize the DNA. FIG. 1 shows results of the method.

Example 3

DNA Extraction in the Presence of Sodium Perchlorate (NaClO$_4$)

Figure 2:
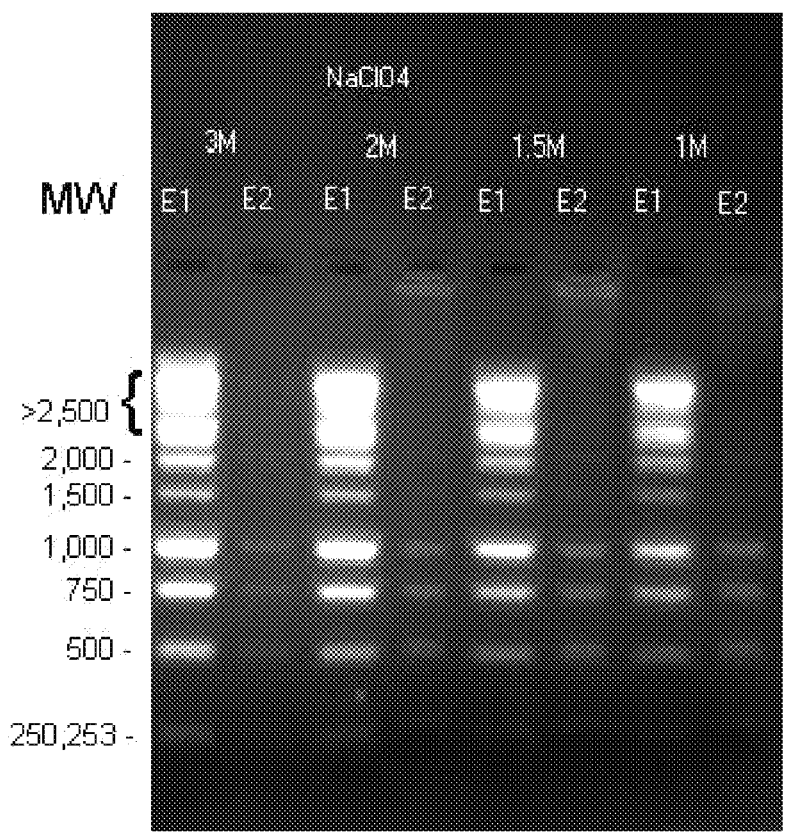
FIG. 2 shows the successful extraction of low base pair DNA from a 1 kb DNA ladder (Promega™) in the presence of sodium perchlorate (NaClO$_4$).

FIG. 2 shows the successful extraction of low base pair DNA from a 1 kb DNA ladder (Promega™) in the presence of sodium perchlorate (NaClO$_4$). The DNA is first bound to silica at various low concentrations of sodium perchlorate as shown in FIG. 2. The supernatant from the first binding solution is subsequently bound to silica at varying sodium perchlorate concentrations, with a finishing high concentration of 4.5 M. These steps are followed by wash and elution steps.

The method can be employed to produce size selective separation of a commercially available DNA ladder with DNA strands ranging in mass from 250 bp to 10,000 bp from normal human plasma in the presence of sodium perchlorate (NaClO$_4$) as the chaotropic salt. The following steps are performed:

1. To four separate vessels, add 10 µL protease solution (20 ug/ul), 200 µL normal human plasma, and 100 µL 4.5 M GuSCN (final concentration 1.45 M).
2. Add NaClO$_4$ to final concentrations of 3M, 2M, 1.5M or 1M. Add 5 µL hydrated silica, 10 µL 1 kb ladder. Mix the solution and incubate 10 minutes at ambient temperature.
3. Centrifuge at 7,000 rpm for 2.5 minutes. Transfer the supernatant to a new vessel. Label the non-target DNA silica as E1 and proceeded to washing step (Step 6).
4. Increase the concentration of the supernatant to 4.5 M NaClO$_4$ for all samples. Add 5 µL of silica, mix and incubate for 10 minutes at ambient temperature.
5. Centrifuge at 7,000 rpm for 2.5 minutes. Discard the supernatant. Label the target DNA silica as E2 and proceeded to washing step (Step 6).
6. Wash pellet 2×500 µL of 1.2 M NaClO$_4$ in 70% ethanol, 1×100 µl ethanol.
7. Air dry silica 5 minutes on low heat.
8. Add 10 µL of 1×TE and incubate at 55 C for 10 minutes.
9. Transfer eluates for E1 and E2 to new tube. Add 2.5 µL bromophenol blue loading buffer, and loaded 10 µL per lane onto a 1.2% agarose gel in 1×TBE. Electrophoresis is used to separate the DNA strands, and ethidium bromide is used to visualize the DNA. FIG. 2 shows results of the method.

Example 4

Adapter-Mediated Ligation of Target Nucleic Acid

Figure 3:
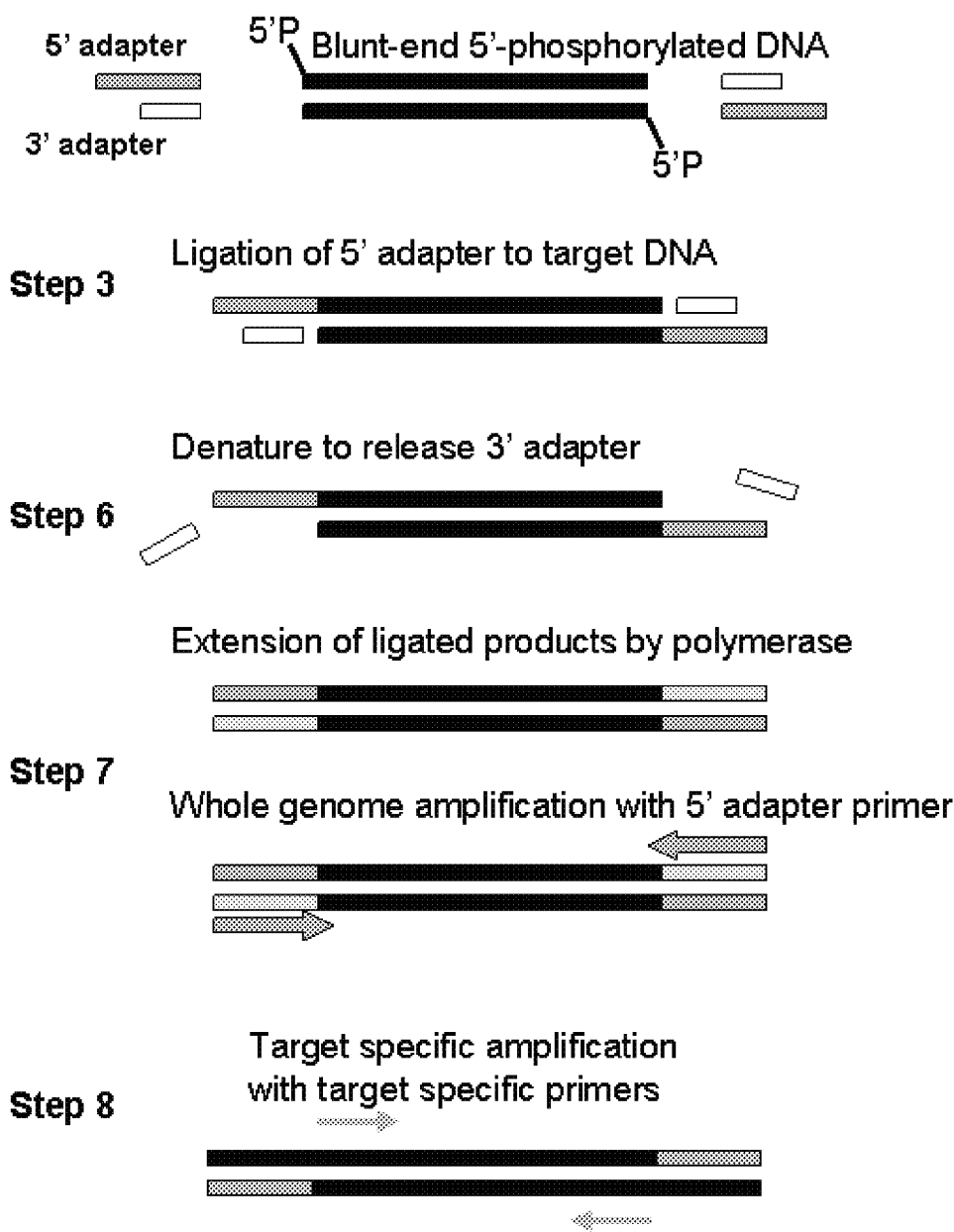
FIG. 3 is a schematic showing the steps of adapter mediated ligation for the selective detection and amplification of target nucleic acids.

The below example provides a procedure, using the method provided herein, to selectively amplify target nucleic acid that is blunt-ended and 5'-phosphorylated. The method relies on the ligation of a non-genome specific adapter to the blunt ends, which allows for whole genome amplification followed by target-specific amplification. While the nature of the termini of all cell-free nucleic acid is unknown, coupling this method with short extension times during amplification will favor the amplification of the oligonucleosome monomer and short multimers. Since the target nucleic acid is shorter than the non-targeted nucleic acid, the target nucleic acid can be enriched over the non-target nucleic acid. This method can be further coupled with specific amplification of a nucleic acid region of interest for further analysis. FIG. 3 shows results of the method.

Exemplary Adapters:

```
                                              (SEQ ID NO: 1)
    5' adapter:    5'-ACACGGCGCACGCCTCCACG-3'

(SEQ ID NO: 2)
    3' adapter:    5'-CGTGGAGGCGTG-3'
```

The 3' adapter is complementary to the 3'-end of 5' adapter to create the blunt-end, double-stranded adapter complex.

```
                                              (SEQ ID NO: 1)
    5' adapter:    5'-ACACGGCGCACGCCTCCACG-3'
                      } blunt-end
                                              (SEQ ID NO: 2)
    3' adapter:    3'-GTGCGGAGGTGC-5'
```

Alternatively, the 3' adapter molecule is modified such that the new sequence consists of 13 nucleobases with a dideoxynucleotide at its 3'-position. This terminator nucleotide does not allow extension of the 3' adapter molecule by any polymerase, thus improving assay efficiency and detection.

Alternative 3' Adapter:

```
                                              (SEQ ID NO: 3)
    3' adapter (SSGA13dd3'):  5'-CGTGGAGGCGTGddNTP-3'
```

The 3' adapter is shorter to reduce the melting temperature and allow for release from the 5' adapter following ligation. Both adapters are non-phosphorylated, and may be made of any sequence that is nonspecific to the nucleic acid to be amplified to prevent non-specific amplification of the genome.

An exemplary procedure is provided below:
1. Prepare total or size selective nucleic acid sample in water or buffer.
2. Add ligation buffer, 5' adapter, 3' adapter, and water to reaction volume.
3. Place the reaction into a thermocycler and heat the reaction to 55° C. for 10 minutes, then slowly ramp down the temperature to 10° C. over 1 hour.
4. Add 1 μl T4 ligase (1-3 U per ul) (or ligation enzyme) and mix well and incubate for 10 min at 10° C., then ramp temperature up to 16° C. and incubate for 10 minutes to over night (12-16 hours).
5. Add 5' primer, 10×PCR buffer, $MgCl_2$, dNTPs, and polymerase.
6. Incubate at 72° C. for 10 minutes (displacement of 3' adapter and initial extension of the ligated sample)
7. Thermocycle for non-template specific amplification

| | |
|---|---|
| Template Denaturation | 10 sec at 94° C. |
| 5' adapter primer annealing | 10 sec at 56° C. |
| 5' adapter primer Extension | 10 sec at 72° C. |
| Final extension | 1 min at 72° C. |
| Hold at 4° C. | |

8. Add template-specific 5' and 3' primers, 10×PCR buffer, $MgCl_2$, dNTPs, and polymerase.
9. Continue with sample to perform target-specific amplification and detection.

Example 5

Rolling-Circle Amplification of Target Nucleic Acid

Described hereafter is a method for intramolecular ligation followed by amplification of a target by inverse PCR or rolling circle amplification to detect a target nucleic acid.

Figure 4:
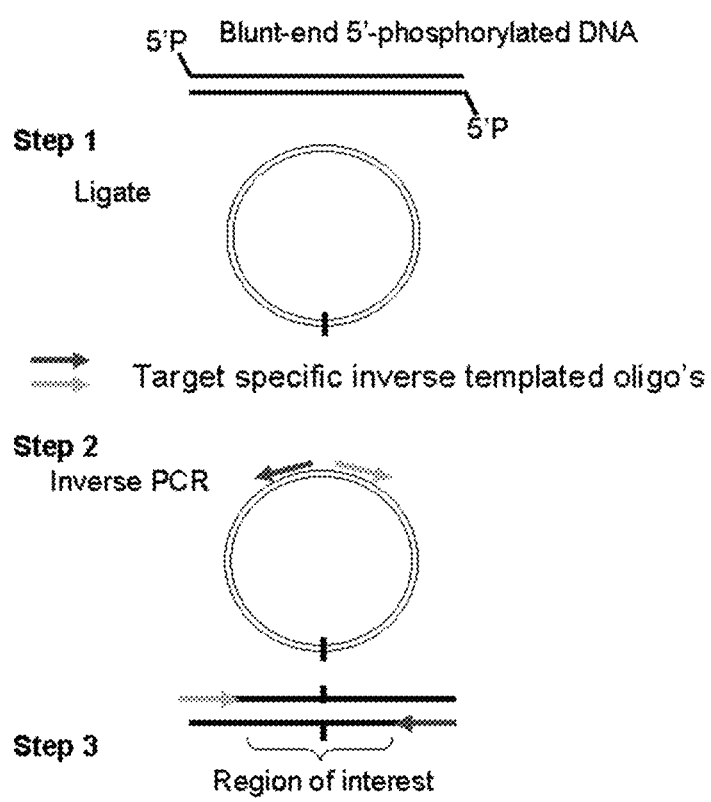
FIG. 4 is a schematic showing the steps of circular ligation and inverse PCR for the selective detection and amplification of target nucleic acids.

Inverse Amplification (See FIG. 4)
1. Prepare total or size selective nucleic acid sample in water or buffer.
2. Add ligation buffer, 1 μL ligase (1-10 U per μL) and water to reaction volume.
3. Mix well and incubate for 10 minutes to over night (12-16 hours) at 4-25° C., followed by ligase inactivation at 65 C for 10 min (or as required for enzyme used).
4. Add PCR buffer, dNTPs, MgCl, inverse PCR primers, and polymerase to the sample.
5. Thermocycle for 45 cycles non-template specific amplification

| | |
|---|---|
| Template Denaturation | 20 sec at 94° C. |
| 5' primer Annealing | 15 sec at 56° C. |
| 5' primer Extension | 10 sec at 72° C. |
| Hold at 4° C. | |

Figure 5:
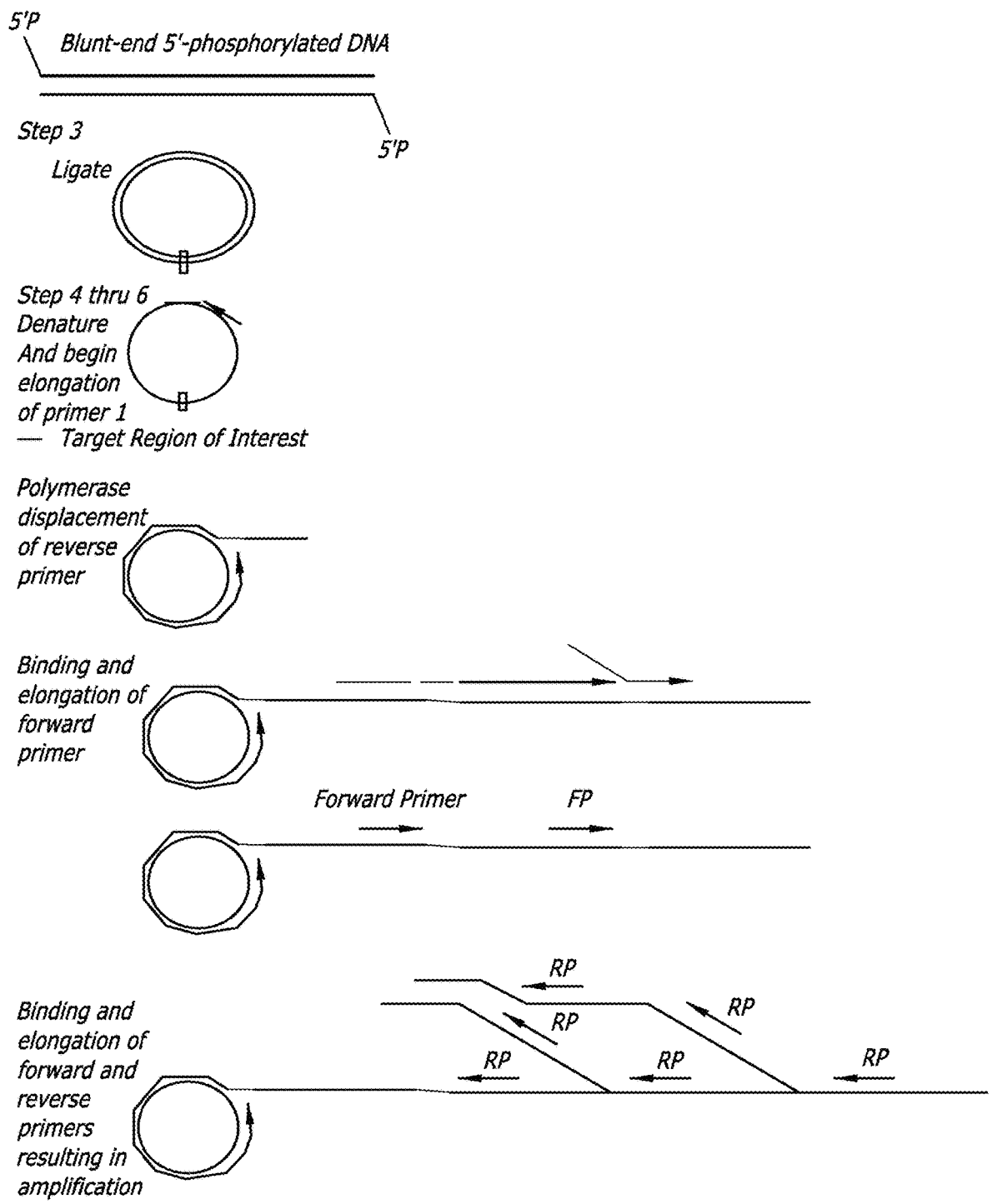
FIG. 5 is a schematic showing the steps of rolling circle amplification (RCA) for the selective detection and amplification of target nucleic acids.

Rolling Circle Amplification (See FIG. 5)
1. Prepare total or size selective nucleic acid sample in water or buffer.
2. Add ligation buffer, 1 μL ligase (1-10 U per μL) and water to reaction volume.
3. Mix well and incubate for 10 minutes to over night (12-16 hours) at 4-25° C., followed by ligase inactivation at 65° C. for 10 min (or as required for enzyme used).
4. Add target specific forward and reverse primers, heat the reaction to 95° C. for 3 minutes to denature the template, then rapidly cool to 4° C. (on ice).
5. Add reaction buffer, dNTP, and strand displacing polymerase (e.g. Templi Phi (Amersham).
6. Elongate at 30° C. for 12 hours or more
7. Stop the reaction by heating to 65° C. for 10 minutes
8. Proceed to detection method The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

What is claimed is:

1. A method for extracting low molecular weight apoptotic DNA from a cell-free DNA sample comprising a mixture of low molecular weight DNA and high molecular weight DNA, which comprises:
   (a) mixing the sample, guanidine (iso)thiocyanate or sodium perchlorate, and a silica solid support comprising silica capable of reversibly binding DNA, thereby forming a first binding solution, wherein the guanidine (iso)thiocyanate or sodium perchlorate is present at 1-4M, at which the high molecular weight DNA selectively adsorbs to the solid support;
   (b) separating the silica solid support from the first binding solution, thereby yielding a fraction separated from the solid support;
   (c) mixing the fraction separated from the silica solid support in (b) with additional guanidine (iso)thiocyanate or sodium perchlorate, whereby the guanidine (iso)thiocyanate or sodium perchlorate is present at a higher concentration than that of the first binding solution in (a);
   (d) introducing additional silica solid support to the mixture in (c), thereby forming a second binding solution, wherein the low molecular weight DNA selectively adsorbs to the additional solid support; and
   (e) separating the additional silica solid support from the second binding solution, thereby extracting low molecular weight DNA from the sample, wherein the low molecular weight DNA comprises less than 1200 base pairs and the high molecular weight DNA comprises 1200 or more base pairs.

2. The method of claim 1, wherein the sample is blood serum, blood plasma or urine.

3. The method of claim 1, further comprising eluting the adsorbed DNA from the separated solid support in (e).

4. The method of claim 2, wherein the blood serum, blood plasma or urine is from a pregnant human.

5. The method of claim 1, wherein the low molecular weight DNA is of fetal origin.

6. The method of claim 1, wherein the high molecular weight DNA is of maternal origin.

7. The method of claim 1, wherein the silica solid support comprises a silica coated magnetic bead.

8. The method of claim 1, wherein the guanidine (iso)thiocyanate or sodium perchlorate of (a) is present at a concentration in the range of 10% to 30% weight and the guanidine (iso)thiocyanate or sodium perchlorate of (c) is present at a concentration in the range of 20% to 60% weight.

* * * * *

UNITED STATES PATENT AND TRADEMARK OFFICE
CERTIFICATE OF CORRECTION

PATENT NO. : 10,662,421 B2
APPLICATION NO. : 15/240692
DATED : May 26, 2020
INVENTOR(S) : Carolyn R. Hoyal-Wrightson, Andreas Braun and Karsten E. Schmidt It is certified that error appears in the above-identified patent and that said Letters Patent is hereby corrected as shown below:

In the Specification

Column 1, Lines 27-28, currently reads:
"Sample," respectively."

Please correct to read as follows:
--Sample."--

In the Claims

Column 25, Line 36-37, Claim 1 currently reads:
"a silica solid support comprising silica"

Please correct to read as follows:
--a silica solid support--

Signed and Sealed this
Fourth Day of August, 2020

Andrei Iancu
*Director of the United States Patent and Trademark Office*

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1

```
acacggcgca cgcctccacg                                                    20

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cgtggaggcg tg                                                            12

<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(13)
<223> OTHER INFORMATION: ddNTP

<400> SEQUENCE: 3
cgtggaggcg tgn                                                           13
```